United States Patent [19]
Curtiss, III et al.

[11] Patent Number: 5,654,184
[45] Date of Patent: Aug. 5, 1997

[54] ORAL IMMUNIZATION BY TRANSGENIC PLANTS

[75] Inventors: Roy Curtiss, III, St. Louis, Mo.; Guy A. Cardineau, Madison, Wis.

[73] Assignee: Washington University, St. Louis, Mo.

[21] Appl. No.: 458,097

[22] Filed: Jun. 1, 1995

Related U.S. Application Data

[60] Division of Ser. No. 398,520, Aug. 29, 1989, which is a continuation-in-part of Ser. No. 240,728, Sep. 6, 1988, abandoned.

[51] Int. Cl.$^6$ .............................. C12N 15/31; C12N 5/10; A01H 5/00; A61K 39/02
[52] U.S. Cl. ................. 435/172.3; 435/69.3; 435/252.3; 435/320.1; 536/23.7; 800/205; 424/93.7; 424/234.1; 424/439; 935/65; 935/67
[58] Field of Search ...................... 435/172.3, 320.1, 435/252.3, 69.3, 240.4; 424/93.7, 234.1, 439; 800/205; 536/23.7; 935/65, 67

[56] References Cited

U.S. PATENT DOCUMENTS

| | | | |
|---|---|---|---|
| 4,771,002 | 9/1988 | Gelvin | 435/172.3 |
| 4,774,182 | 9/1988 | Syzbalski | 435/172.3 |
| 4,784,949 | 11/1988 | Gelfand | 435/172.3 |
| 4,894,332 | 1/1990 | Schaller et al. | 435/172.3 |

FOREIGN PATENT DOCUMENTS

| | | |
|---|---|---|
| 0060129 | 9/1982 | European Pat. Off. . |
| 0080806 | 6/1983 | European Pat. Off. . |
| 0168322 | 1/1986 | European Pat. Off. . |
| 8606635 | 11/1986 | WIPO . |
| 8700865 | 2/1987 | WIPO . |

OTHER PUBLICATIONS

Kovgan, A.A., V.M. Zhdanov (1989) "Potential vector for introducing animal virus genes into cells of higher plants" Biotekhnologiya 5(2):148–154, **abstract No. 207160n, Chemical Abstracts 110:225.
Aizpurua et al 1988 (Feb.) J. Exp. Med. 167: 440–451.
Clements et al 1986 Infection and Immunity 53: 685–692.
Dallas et al 1980 Nature 288: 499–501.
Holt et al 1982 Infection and Immunity 38: 147–156.

*Primary Examiner*—Patricia R. Moody
*Attorney, Agent, or Firm*—Saliwanchik, Lloyd & Saliwanchik

[57] ABSTRACT

The invention is directed to transgenic plants expressing colonization and/or virulence antigens specified by genes from pathogenic microorganisms. It is also directed to the use of such transgenic plants for oral immunization of humans and other animals to elicit a secretory immune response which inhibits colonization of or invasion by such pathogenic microorganisms through a mucosal surface of humans or other animals.

5 Claims, 15 Drawing Sheets

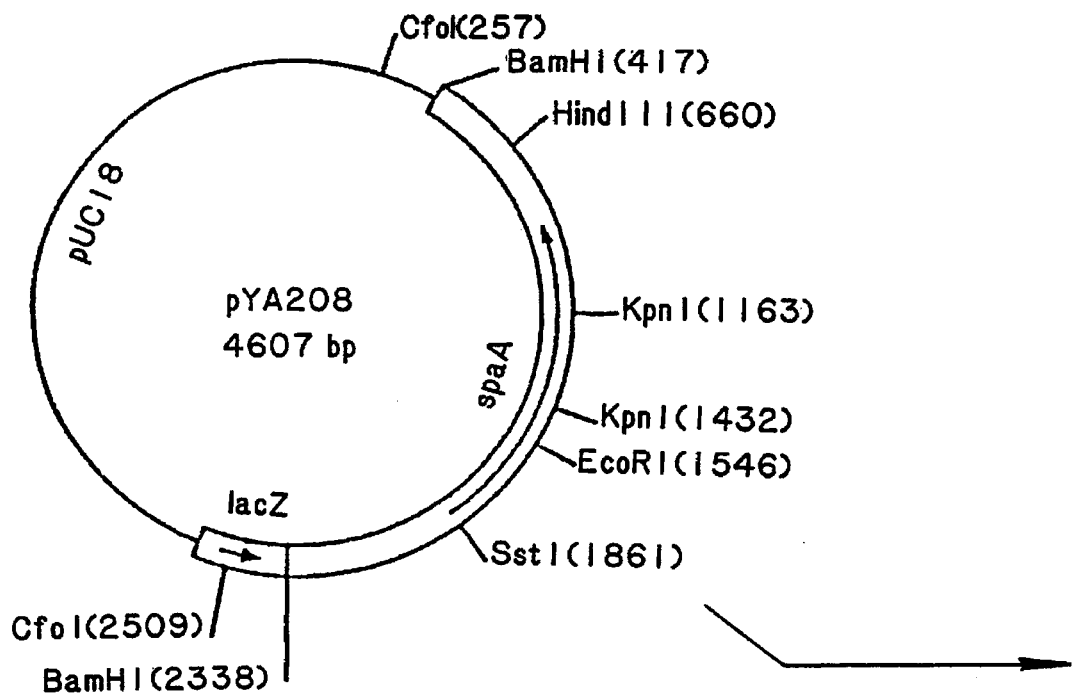
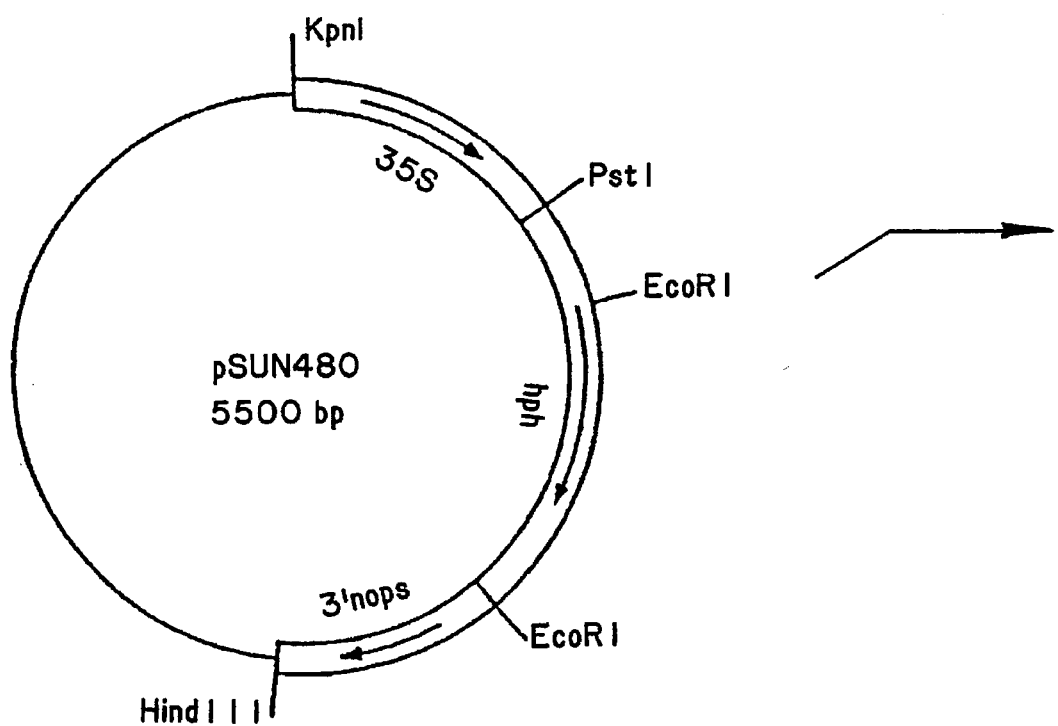
FIG. 6A

FIG. 8A pSUN387    4643 BP

ORIGIN    ECO RI SITE UPSTREAM OF ASD PROMOTER

```
   1 GAATTCAATA GTTTATGGAC TTTTTTTTTG TATAAAAAGT
  41 AGTATAATGT CTATTATTAG AATGAATTAG GGTACCGATG
  81 TTCACCACTG ATAATGAGAA GATTAGCCTT TTCAATTTCA
 121 GAAAGAATGC TAACCCACAG ATGGTTAGAG AGGCTTACGC
 161 AGCAGGTCTC ATCAAGACGA TCTACCCGAG CAATAATCTC
 201 CAGGAGATCA AATACCTTCC CAAGAAGGTT AAAGATGCAG
 241 TCAAAAGATT CAGGACTAAC TGCATCAAGA ACACAGAGAA
 281 AGATATATTT CTCAAGATCA GAAGTACTAT TCCAGTATGG
 321 ACGATTCAAG GCTTGCTTCA CAAACCAAGG CAAGTAATAG
 361 AGATTGGAGT CTCTAAAAAG GTAGTTCCCA CTGAATCAAA
 401 GGCCATGCAT GGAGTCAAAG ATTCAAATAG AGGACCTAAC
 441 AGAACTCGCC GTAAAGACTG GCGAACAGTT CATACAGAGT
 481 CTCTTACGAC TCAATGACAA GAAGAAAATC TTCGTCAACA
 521 TGGTGGAGCA CGACACGCTT GTCTACTCCA AAAATATCAA
 561 AGATACAGTC TCAGAAGACC AAAGGGCAAT TGAGACTTTT
 601 CAACAAAGGG TAATATCCGG AAACCTCCTC GGATTCCATT
 641 GCCCAGCTAT CTGTCACTTT ATTGTGAAGA TAGTGGAAAA
 681 GGAAGGTGGC TCCTACAAAT GCCATCATTG CGATAAAGGA
 721 AAGGCCATCG TTGAAGATGC CTCTGCCGAC AGTGGTCCCA
 761 AAGATGGACC CCCACCCACG AGGAGCATCG TGGAAAAAGA
 801 AGACGTTCCA ACCACGTCTT CAAAGCAAGT GGATTGATGT
 841 GATCAACATG GTGGAGCACG ACACGCTTGT CTACTCCAAA
 881 AATATCAAAG ATACAGTCTC AGAAGACCAA AGGGCAATTG
 921 AGACTTTTCA CAAAGGGTA ATATCCGGAA ACCTCCTCGG
 961 ATTCCATTGC CCAGCTATCT GTCACTTTAT TGTGAAGATA
1001 GTGGAAAAGG AAGGTGGCTC CTACAAATGC CATCATTGCG
1041 ATAAAGGAAA GGCCATCGTT GAAGATGCCT CTGCCGACAG
1081 TGGTCCCAAA GATGGACCCC CACCCACGAG GAGCATCGTG
1121 GAAAAGAAG ACGTTCCAAC CACGTCTTCA AAGCAAGTGG
1161 ATTGATGTGA TATCTCCACT GACGTAAGGG ATGACGCACA
1201 ATCCCACTAT CCTTCGCAAG ACCCTTCCTC TATATAAGGA
1241 AGTTCATTTC ATTTGGAGAG GACACGGGGA TCGCGGTACC
1281 CTAAGGAGGT GACAGCCATG GATCCTCTAG AGTCGACCTG
1321 CAGGAATTCG GTCGAAGCAG ATCGTTCAAA CATTTGGCAA
1361 TAAAGTTTCT TAAGATTGAA TCCTGTTGCC GGTCTTGCGA
1401 TGATTATCAT ATAATTTCTG TTGAATTACG TTAAGCATGT
1441 AATAATTAAC ATGTAATGCA TGACGTTATT TATGAGATGG
1481 GTTTTTATGA TTAGAGTCCC GCAATTATAC ATTTAATACG
1521 CGATAGAAAA CAAATATAG CGCGCAAACT AGGATAAATT
1561 ATCGCGCGCG GTGTCATCTA TGTTACTAGA TCGATCAAAC
1601 TTCGGTACTG TGTAATGACG ATGAGCAATC GAGAGGCTGA
1641 CTAACAAAAG GTATGCCCAA AAACAACCTC TCCAAACTGT
1681 TTCGAATTGG AAGTTTCTGC TCATGCCGAC AGGCATAACT
1721 TAGATATTCG CGGGCTATTC CCACTAATTC GTCCTGCTGG
1761 TTTGCGCCAA GATAAATCAG TGCATCTCCT TACAAGTTCC
1801 TCTGTCTTGT GAAATGAACT GCTGACTGCC CCCAAGAAA
1841 GCCTCCTCAT CTCCCAGTTG GCGGCGGCTG ATACACCATC
1881 GAAACCCAC GTCCGAACAC TTGATACATG TGCCTGAGAA
1921 ATAGGCCTAC GTCCAAGAGC AAGTCCTTTC TGTGCTCGTC
1961 GGAAATTCCT CTCCTGTCAG ACGGTCGTGC GCATGTCTTG
2001 CGTTGATGAA GCTTGGCACT GGCCGTCGTT TTACAACGTC
2041 GTGACTGGGA AAACCCTGGC GTTACCCAAC TTAATCGCCT
```

FIG. 8B

```
2081 TGCAGCACAT CCCCCCTTCG CCAGCTGGCG TAATAGCGAA
2121 GAGGCCCGCA CCGATCGCCC TTCCCAACAG TTGCGTAGCC
2161 TGAATGGCGA ATGGCGCCTG ATGCGGTATT TTCTCCTTAC
2201 GCATCTGTGC GGTATTTCAC ACCGCATATG GTGCACTCTC
2241 AGTACAATCT GCTCTGATGC CGCATAGTTA AGCCAGCCCC
2281 GACACCCGCC AACACCCGCT GACGCGCCCT GACGGGCTTG
2321 TCTGCTCCCG GCATCCGCTT ACAGACAAGC TGTGACCGTC
2361 TCCGGGAGCT GCATGTGTCA GAGGTTTTCA CCGTCATCAC
2401 CGAAACGCGC GAGACGAAAG GGCCTCGTGA TACGCCTATT
2441 TTTATAGGTT AATGTCATGA TAATAATGGT TTCTTAGACG
2481 TCAGGTGGCA CTTTTCGGGG AAATGTGCGC GGAACCCCTA
2521 TTTGTTTATT TTTCTAAATA CATTCAAATA TGTATCCGCT
2561 CATGAGACAA TAACCCTGAT AAATGCTTCA ATAATATTGA
2601 AAAAGGAAGA GTATGAGTAT TCAACATTTC CGTGTCGCCC
2641 TTATTCCCTT TTTTGCGGCA TTTTGCCTTC CTGTTTTTGC
2681 TCACCCAGAA ACGCTGGTGA AAGTAAAAGA TGCTGAAGAT
2721 CAGTTGGGTG CACGAGTGGG TTACATCGAA CTGGATCTCA
2761 ACAGCGGTAA GATCCTTGAG AGTTTTCGCC CCGAAGAACG
2801 TTTTCCAATG ATGAGCACTT TTAAAGTTCT GCTATGTGGC
2841 GCGGTATTAT CCCGTATTGA CGCCGGGCAA GAGCAACTCG
2881 GTCGCCGCAT ACACTATTCT CAGAATGACT TGGTTGAGTA
2921 CTCACCAGTC ACAGAAAAGC ATCTTACGGA TGGCATGACA
2961 GTAAGAGAAT TATGCAGTGC TGCCATAACC ATGAGTGATA
3001 ACACTGCGGC CAACTTACTT CTGACAACGA TCGGAGGACC
3041 GAAGGAGCTA ACCGCTTTTT TGCACAACAT GGGGGATCAT
3081 GTAACTCGCC TTGATCGTTG GGAACCGGAG CTGAATGAAG
3121 CCATACCAAA CGACGAGCGT GACACCACGA TGCCTGTAGC
3161 AATGGCAACA ACGTTGCGCA AACTATTAAC TGGCGAACTA
3201 CTTACTCTAG CTTCCCGGCA ACAATTAATA GACTGGATGG
3241 AGGCGGATAA AGTTGCAGGA CCACTTCTGC GCTCGGCCCT
3281 TCCGGCTGGC TGGTTTATTG CTGATAAATC TGGAGCCGGT
3321 GAGCGTGGGT CTCGCGGTAT CATTGCAGCA CTGGGGCCAG
3361 ATGGTAAGCC CTCCCGTATC GTAGTTATCT ACACGACGGG
3401 GAGTCAGGCA ACTATGGATG AACGAAATAG ACAGATCGCT
3441 GAGATAGGTG CCTCACTGAT TAAGCATTGG TAACTGTCAG
3481 ACCAAGTTTA CTCATATATA CTTTAGATTG ATTTAAAACT
3521 TCATTTTTAA TTTAAAAGGA TCTAGGTGAA GATCCTTTTT
3561 GATAATCTCA TGACCAAAAT CCCTTAACGT GAGTTTTCGT
3601 TCCACTGAGC GTCAGACCCC GTAGAAAAGA TCAAAGGATC
3641 TTCTTGAGAT CCTTTTTTTC TGCGCGTAAT CTGCTGCTTG
3681 CAAACAAAAA AACCACCGCT ACCAGCGGTG GTTTGTTTGC
3721 CGGATCAAGA GCTACCAACT CTTTTTCCGA AGGTAACTGG
3761 CTTCAGCAGA GCGCAGATAC CAAATACTGT CCTTCTAGTG
3801 TAGCCGTAGT TAGGCCACCA CTTCAAGAAC TCTGTAGCAC
3841 CGCCTACATA CCTCGCTCTG CTAATCCTGT TACCAGTGGC
3881 TGCTGCCAGT GGCGATAAGT CGTGTCTTAC CGGGTTGGAC
3921 TCAAGACGAT AGTTACCGGA TAAGGCGCAG CGGTCGGGCT
3961 GAACGGGGGG TTCGTGCACA CAGCCCAGCT TGGAGCGAAC
4001 GACCTACACC GAACTGAGAT ACCTACAGCG TGAGCATTGA
4041 GAAAGCGCCA CGCTTCCCGA AGGGAGAAAG GCGGACAGGT
4081 ATCCGGTAAG CGGCAGGGTC GGAACAGGAG AGCGCACGAG
4121 GGAGCTTCCA GGGGGAAACG CCTGGTATCT TTATAGTCCT
4161 GTCGGGTTTC GCCACCTCTG ACTTGAGCGT CGATTTTTGT
4201 GATGCTCGTC AGGGGGGCGG AGCCTATGGA AAAACGCCAG
4241 CAACGCGGCC TTTTTACGGT TCCTGGCCTT TTGCTGGCCT
4281 TTTGCTCACA TGTTCTTTCC TGCGTTATCC CCTGATTCTG
```

FIG. 8C

```
4321 TGGATAACCG TATTACCGCC TTTGAGTGAG CTGATACCGC
4361 TCGCCGCAGC CGAACGACCG AGCGCAGCGA GTCAGTGAGC
4401 GAGGAAGCGG AAGAGCGCCC AATACGCAAA CCGCCTCTCC
4441 CCGCGCGTTG GCCGATTCAT TAATGCAGCT GGCACGACAG
4481 GTTTCCCGAC TGGAAAGCGG GCAGTGAGCG CAACGCAATT
4521 AATGTGAGTT ACCTCACTCA TTAGGCACCC CAGGCTTTAC
4561 ACTTTATGCT TCCGGCTCGT ATGTTGTGTG GAATTGTGAG
4601 CGGATAACAA TTTCACACAG GAAACAGCTA TGACCATGAT
4641 TAC
```

ORAL IMMUNIZATION BY TRANSGENIC PLANTS

This is a division of application Ser. No. 07/398,520, filed 29 Aug. 1989, which is a continuation-in-part of application Ser. No. 07/240,728, filed 6 Sep. 1988 (now abandoned).

BACKGROUND OF THE INVENTION

Advances in recombinant DNA technology coupled with advances in plant transformation and regeneration technology have made it possible to introduce new genetic material into plant cells, plants or plant tissue, thus introducing new traits, eg., phenotypes, that enhance the value of the plant or plant tissue. The present invention relates to the introduction into plants of genes encoding colonization or virulence antigens or parts thereof of pathogens which colonize on or invade through mucosal surfaces of animal species. The present invention also relates to production of such colonization or virulence antigen or parts thereof by the plants. The invention further relates to the use of plant matter containing such colonization or virulence antigen or parts thereof for the oral immunization of humans and other animals to inhibit infection of the animal or human by the pathogen.

A. General Overview of Infectious Diseases and Immunity

Infectious diseases are becoming an increasing problem for both animal and human health. Gillespie J. et al., *Infectious Diseases of Domestic Animals*, Comstock Press, Ithaca, N.Y. (1981); Mandell, G. L. et al., *Principles and Practices of Infectious Diseases*, 2nd Ed., John Wiley and Sons, New York (1985). Diseases caused by bacterial pathogens are particularly troublesome due to the increase in antibiotic-resistant pathogens. Most pathogens enter on or through a mucosal surface, with the exception of the insect-borne pathogens or those which enter the body through a wound. The former pathogens include, but are not limited to, pathogenic species in the bacterial genera *Actinomyces, Aeromonas, Bacillus, Bacteroides, Bordetella, Brucella, Campylobacter, Capnocytophaga, Clamydia, Clostridium, Corynebacterium, Eikenella, Erysipelothrix, Escherichia, Fusobacterium, Hemophilus, Klebsiella, Legionella, Leptospira, Listeria, Mycobacterium, Mycoplasma, Neisseria, Nocardia, Pasteurella, Proteus, Pseudomonas, Rickettsia, Salmonella, Selenomonas, Shigella, Staphylococcus, Streptococcus, Treponema, Vibrio,* and *Versinia*, pathogenic viral strains from the groups Adenovirus, Coronavirus, Herpesvirus, Orthomyxovirus, Picornovirus, Poxvirus, Reovirus, Retrovirus, Rotavirus, pathogenic fungi from the genera *Aspergillus, Blastomyces, Candida, Coccidiodes, Cryptococcus, Histoplasma* and *Phycomyces,* and pathogenic parasites in the genera *Eimeria, Entamoeba, Giardia,* and *Trichomonas*. It is generally acknowledged that prevention of infectious diseases would be much more cost-effective than attempts to treat infections once they occur. Thus, increased attention is being addressed to the development of vaccines for the effective immunization of humans and other animals. Germanier, R., *Bacterial Vaccines*, Academic Press, London (1984); Brown, F., *Ann. Rev. Microbiol.* 38, 221 (1984).

Animal and human hosts infected by a pathogen mount an immune response in an attempt to overcome the pathogen. There are three branches of the immune system: mucosal, humoral and cellular. Hood, L. E. et al., *Immunology*, 2 nd Ed., Benjamin Publishing Co., Menlo Park, Calif. (1984).

Mucosal immunity results from the production of secretory IgA (sIgA) antibodies in secretions that bathe all mucosal surfaces of the respiratory tract, gastrointestinal tract and the genitourinary tract and in secretions from all secretory glands. McGhee, J. R. et al.,*Annals N.Y. Acad. Sci.* 409, (1983). These sIgA antibodies act to prevent colonization of pathogens on a mucosal surface (Williams, R. C. et al., *Science* 177, 697 (1972); McNabb, P. C. et al., *Ann. Rev. Microbiol.* 35, 477 (1981) and thus act as a first line of defense to prevent colonization or invasion through a mucosal surface. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT). Cebra, J. J. et al., *Cold Spring Harbor Symp. Quant. Biol.* 41, 210 (1976); Bienenstock, J. M., *Adv. Exp. Med. Biol.* 107, 53 (1978); Weisz-Carrington, P. Et al., *J. Immunol* 123, 1705 (1979); McCaughan, G. et al., *Internal Rev. Physiol* 28, 131 (1983). Membranous microfold cells, otherwise known as M Cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body. Cebra et al., supra; Bienenstock et al., supra; Weinz-Carrington et al., supra; McCaughan et al., supra. Oral immunization is therefore a most important route to stimulate a generalized mucosal immune response and, in addition, leads to local stimulation of a secretory immune response in the oral cavity and in the gastrointestinal tract.

Humoral immunity results from production of IgG and IgM in serum and potentiates phagocytosis of pathogens, the neutralization of viruses, or complement-mediated cytotoxicity of pathogens (Hood et al., supra). The immunity to a pathogen can be transmitted from the mother to the offspring in both birds and mammals by delivery of the secretory antibody either in the egg or in the colostrum or by placental transfer of serum antibody in the case of mammals. McGhee et al., supra, McNabb et al., supra; Mestecky, J., *J. Clin. Immunol.,* 7, 265 (1987).

Cellular immunity is of two types: One is termed a delayed-type hypersensitivity response which causes T lymphocytes to stimulate macrophages to kill bacterial, parasitic, and mycotic pathogens. In the other type, cytotoxic T lymphocytes are directed to kill host cells infected with viruses. Hood, et al. supra.

Secretory IgA antibodies directly inhibit the adherence of microorganisms to mucosal epithelial cells and to the teeth of the host. Abraham, S. N. et al., *Advances in Host Defense Mechanisms,* Raven Press, N.Y., 4, 63 (1985). Liljemark, W. F. et al., *Infect. Immun.* 26, 1104 (1979). Reinholdt, J. et al., *J. Dent. Res.* 66, 492 (1987). This may be done by agglutination of microorganisms, reduction of hydrophobicity, Magnusson, K. E., et al., *Immunology* 36, 439 (1979), or negative charge and blockage of microbial adhesions. These anti-adherence effects are amplified by other factors such as secretory glycoproteins, continuous desquamation of surface epithelium and floral competition. Abraham, S. N. et al., supra. Shedlofsky, S. et al., *J. Infect. Dis.* 129, 296 (1974). For example, oral immunization against inactivated *Vibrio* cholerae to induce a secretory immune response results in a 10-to 30- fold decrease in intestinal numbers.

Clinical experience with human peroral poliovirus vaccine and several peroral or intranasal virus vaccines applied in veterinary medicine shows that sIgA plays a decisive role in protective effect by the mucosal immune system against respiratory and enteric viral infections. Rusel-Jones, G. J. et al., *Int. Arch. Allergy Appl. Immunol.* 66, 316 (1981). Ogra, P. L. et al., In J. Bienenstock (ed), *Immunology of the Lung and Upper Respiratory Tract.* McGraw-Hill, N.Y. 242 (1984). The effect of sIgA appears to be that of inhibiting the entry of viruses into host cells rather than prevention of attachment. Taylor, H. P. et al., *J. Exp. Med.* 161, 198 (1985). Kilian, M. et al., *Microbiol. Rev.* 52, 296 (1988).

B. General Overview of Plant Transformation

Various methods are known in the art to accomplish the genetic transformation of plants and plant tissues (i.e., the stable introduction of foreign DNA into plants). These include transformation by *Agrobacterium* species and transformation by direct gene transfer.

1. Agrobacterium-mediated Transformation

*A. tumefaciens* is the etiologic agent of crown gall, a disease of a wide range of dicotyledons and gymnosperms, DeCleene, M. et al., *Bot. Rev.* 42, 389 (1976), that results in the formation of tumors or galls in plant tissue at the site of infection. *Agrobacterium*, which normally infects the plant at wound sites, carries a large extrachromosomal element called the Ti (tumor-inducing) plasmid.

Ti plasmids contain two regions required for tumorigenicity. One region is the T-DNA (transferred-DNA) which is the DNA sequence that is ultimately found stably transferred to plant genomic DNA. The other region required for tumorigenicity is the vir (virulence) region which has been implicated in the transfer mechanism. Although the vir region is absolutely required for stable transformation, the vir DNA is not actually transferred to the infected plant. Chilton, M-D. et al., *Cell* 11, 263 (1977), Thomashow, M. F. et al., *Cell* 19, 729 (1980). Transformation of plant cells mediated by infection with *A. tumefaciens* and subsequent transfer of the T-DNA alone have been well documented. See, for example, Bevan, M. W. et al., *Int. Rev. Genet.* 16, 357 (1982).

After several years of intense research in many laboratories, the *Agrobacterium* system has been developed to permit routine transformation of a variety of plant tissue. See, for example, Schell, J. et al., *Bio/Technology* 1, 175 (1983); Chilton, M-D, *Scientific American* 248, 50 (1983). Representative tissues transformed in this manner include tobacco, Barton, K. A. et al., *Cell* 32, 1033 (1983); tomato, Fillatti, J. et al., *Bio/Technology* 5, 726 (1987); sunflower, Everett, N. P. et al., *Bio/Technology* 5, 1201 (1987); cotton, Umbeck, P. et al., *Bio/Technology* 5, 263 (1987); rapeseed, Pua, E. C. et al., *Bio/Technology* 5, 815 (1987); potato, Facciotti D. et al., *Bio/Technology* 3, 241 (1985); poplar, Pythoud, F. et al., *Bio/Technology* 5, 1323 (1987); and soybean, Hinchee, M. A. et al., *Bio/Technology* 6, 915 (1988).

*Agrobacterium rhizogenes* has also been used as a vector for plant transformation. That bacterium, which incites root hair formation in many dicotyledonous plant species, carries a large extrachromosomal element called an Ri (root-inducing) plasmid which functions in a manner analogous to the Ti plasmid of *A. tumefaciens*. Transformation using *A. rhizogenes* has developed analogously to that of *A. tumefaciens* and has been successfully utilized to transform, for example, alfalfa, Sukhapinda, K. et al., *Plant Mol. Biol.* 8, 209 (1987); *Solanum nigrum* L., Wei Z-H, et al., *Plant Cell Reports* 5, 93(1986); and, poplar, Pythoud, et al., supra.

2. Direct Gene Transfer

Several so-called direct gene transfer procedures have been developed to transform plants and plant tissues without the use of an *Agrobacterium* intermediate. In the direct transformation of protoplasts the uptake of exogenous genetic material into a protoplast may be enhanced by use of a chemical agent or electric field. The exogenous material may then be integrated into the nuclear genome. The early work was conducted in the dicot *Nicotiana tabacum* (tobacco) where it was shown that the foreign DNA was incorporated and transmitted to progeny plants. Paszkowski, J. et al., *EMBO J*, 3, 2717 (1984); and Potrykus, I. et al., *Mol. Gen. Genet.* 199, 169 (1985).

Monocot protoplasts have also been transformed by this procedure: for example, *Triticum monococcum*, Lorz H. et al., *Mol. Gen. Genet.* 199, 178 (1985); *Lolium multiflorum* (Italian ryegrass), Potrykus, I. et al., *Mol. Gen. Genet* 199, 183 (1985); maize, Rhodes, C., et al., *Bio/Technology* 5, 56 (1988); and Black Mexican sweet corn, Fromm, M. et al., *Nature* 319, 791 (1986).

Introduction of DNA into protoplasts of *N. tabacum* is effected by treatment of the protoplasts with an electric pulse in the presence of the appropriate DNA in a process called electroporation. Fromm, M. E., in *Methods in Enzymology*, eds. Wu, R. and Grossman, L., Academic Press, Orlando, Fla., Volume 153, 307 (1987) and Shillito, R. D. and Potrykus, I. in *Methods in Enzymology*, eds., Wu, R. and Grossman, L., Academic Press, Orlando, Fla. Volume 153, 283 (1987). Protoplasts are isolated and suspended in a mannitol solution. Supercoiled or circular plasmid DNA is added. The solution is mixed and subjected to a pulse of about 400 Vcm at room temperature for less than 10 to 100 μ sec. A reversible physical breakdown of the membrane occurs to permit DNA uptake into the protoplasts.

DNA viruses have been used as gene vectors. A cauliflower mosaic virus carrying a modified bacterial methotrexate-resistance gene was used to infect a plant. The foreign gene was systematically spread in the plant. Brisson, N. et al., *Nature* 310, 511 (1984). The advantages of this system are the ease of infection, systematic spread within the plant, and multiple copies of the gene per cell.

Liposome fusion has also been shown to be a method for transformation of plant cells. Protoplasts are brought together with liposomes carrying the desired gene. As membranes merge, the foreign gene is transferred to the protoplast. Dehayes, A. et al., *EMBO J.* 4, 2731 (1985).

Polyethylene glycol (PEG) mediated transformation has been carried out in *N. tabacum* a dicot, and *Lolium multiflorum*, a monocot. It is a chemical procedure of direct gene transfer based on synergistic interaction between $Mg^{2+}$, PEG, and possibly $Ca^{2+}$. Negrutiu, R. et al., *Plant Mol. Biol.* 8, 363 (1987).

Alternatively, exogenous DNA can be introduced into cells or protoplasts by microinjection. A solution of plasmid DNA is injected directly into the cell with a finely pulled glass needle. In this manner, alfalfa protoplasts have been transformed by a variety of plasmids, Reich, T. J. et al., *Bio/Technology* 4, 1001 (1986).

A more recently developed procedure for direct gene transfer involves bombardment of cells by microprojectiles carrying DNA. Klein, T. M. et al., *Nature* 327, 70 (1987). In this procedure called particle acceleration, tungsten or gold particles coated with the exogenous DNA are accelerated toward the target cells. At least transient expression has been achieved in onion. This procedure has been utilized to introduce DNA into Black Mexican sweet corn cells in suspension culture and maize immature embryos and also into soybean protoplasts. Klein, T. M. et al., *Bio/Technology* 6, 559 (1988). McCabe, D. E. et al., *Bio/Technology* 6, 923 (1988). Stably transformed cultures of maize and tobacco have been obtained by microprojectile bombardment. Klein, T. M. et al (1988), supra. Stably transformed soybean plants have been obtained by this procedure. McCabe, D. E. et al., supra.

C. General Overview of Plant Regeneration

Just as there are a variety of methods for the transformation of plant tissue, there are a variety of methods for the regeneration of plants from plant tissue. The particular method of regeneration will depend on the starting plant tissue and the particular plant species to be regenerated. In recent years, it has become possible to regenerate many species of plants from callus tissue derived from plant explants. The plants which can be regenerated from callus include monocots, such as corn, rice, barley, wheat and rye, and dicots, such as sunflower, soybean, cotton, rapeseed and tobacco.

Regeneration of plants from tissue transformed with *A. tumefaciens* has been demonstrated for several species of plants. These include sunflower, Everett, N. P. et al., supra; tomato, Fillatti, J. J. et al., supra; white clover, White, D. W. R. et al., *Plant Mol. Biol.* 8, 461 (1987); rapeseed, Pua, E-C. et al., supra; cotton, Umbeck, P. et al., supra; tobacco, Horsch, R. B. et al., *Science* 225, 1229 (1985) and Hererra-Estrella, L. et al., *Nature* 303, 209 (1983); and poplar, Pythoud et al., supra. The regeneration of alfalfa from tissue transformed with *A. rhizogenes* has been demonstrated by Sukhapinda, K. et al., supra.

Plant regeneration from protoplasts is a particularly useful technique. See Evans, D. A. et al., *Handbook of Plant Cell Culture* 1, 124 (1983). When a plant species can be regenerated from protoplasts, then direct gene transfer procedures can be utilized, and transformation is not dependent on the use of *A. tumefaciens*. Regeneration of plants from protoplasts has been demonstrated for rice, Abdullah, R. et al., *Bio/Technology* 4, 1087 (1987); tobacco, Potrykus, I. et al., supra; rapeseed, Kansha, et al., *Plant Cell Reports* 5, 101 (1986); potato, Tavazza, R. et al., *Plant Cell Reports* 5, 243 (1986); eggplant, Sihackaki, D. et al., *Plant Cell, Tissue, Organ Culture* 11, 179 (1987); cucumber, Jia S-R,. et al., *J. Plant Physiol.* 124, 393 (1986); poplar, Russel, J. A. et al., *Plant Sci.* 46, 133 (1986); corn, Rhodes, C. et al., supra; and soybean, McCabe, D. E. et al., supra.

D. Means For Inducing a Secretory Immune Response

The M cells overlying the Peyer's patches of the gut-associated lymphoid tissue (GALT) are capable of taking up a diversity of antigenic material and particles (Sneller, M. C. and Strober, W., *J. Inf. Dis.* 154, 737 (1986). Because of their abilities to take up latex and polystyrene spheres, charcoal, microcapsules and other soluble and particulate matter, it is possible to deliver a diversity of materials to the GALT independent of any specific adhesive-type property of the material to be delivered. In this case, antigen delivery to the GALT leads to a generalized mucosal immune response with sIgA production against the antigen on all mucosal surfaces and by all secretory glands. One can also stimulate a local secretory immune response by antigen delivery to a mucosal surface or to a secretory gland. The mechanism(s) for generating such a localized secretory immune response is(are) poorly understood. Recent evidence, Black, R. E. et al. *Infect. Immun.* 55,1116 (1987); Elson, C. O., in *Curr. Top. Microbiol. Immunol.* 146, 29 (1989), indicate that the B subunit of cholera toxin when administered orally with an antigen serves as an adjuvant to enhance the protective immune response. It therefore follows, since the B subunit of cholera toxin as well as of the *E. coli* heat-labile enterotoxin are capable of attaching to the GM-1 ganglioside of the intestinal epithelium and causing translocation across the epithelial membrane, that such pilot or targeting proteins might be important in eliciting a local secretory immune response.

It is of course possible to consider fusing a gene for a given colonization and/or virulence antigen to an N-terminal or C-terminal sequence specifying the B subunit of cholera toxin, the B subunit of heat-labile enterotoxin, Yamamoto, T. et al. *J. Biol. Chem.* 259, 5037 (1984), the PapG protein adhesion that specifically binds to α-D-galactopyranosyl-(1, 4)-β-D-galactopyranoside, Lund, B. et al., *Proc. Natl. Acad. Sci.* USA 84, 5898 (1987), or the invasions causing penetration of bacteria through epithelial cell membranes as identified in and cloned from *Yersinia pseudotuberculosis*, Isberg, R. R., et al. Cell 50, 769 (1987), *Shigella* and *Salmonella*. Galan, J. et al., *Poc. Natl. Acad. Sci.* U.S.A. 86, 6383 (1989); Curtiss, R. III et al., in *Curr. Top. Microbiol. Immunol.* 146, 35 (1989). In each case, it can be anticipated that the product of the gene fusion will be more readily transported into cells of the intestinal mucosa and lead to enhanced local secretory immune responses. It is also possible that this form of gene fusion would facilitate uptake and presentation of antigens to the GALT. The production of sIgA against a particular antigen can also be further enhanced by the addition of orally-administered adjuvants, such as microbial cell wall constituents Michalek, S. M. et al., in *Curr. Top. Microbiol. Immunol.* 146, 51 (1989).

It is therefore evident that stimulation of a specific sIgA respone of a both local and generalized nature can be achieved by oral immunization with purified proteins, Taubman, M. A. and D. J. Smith, in *Curr. Top. Microbiol. Immunol.* 146, 187 (1989), microencapsulated microbial products and viruses, Eldridge, J. H. et al., in *Curr. Top. Microbiol. Immunol.* 146, 59 (1989), whole-killed bacteria, Michalek et al., *Science* 191, 1238 (1976), and by ingestion of live attenuated viruses, Cebra, et al., supra, and bacteria, Curtiss, R. III et al., in *Proceedings of the Tenth International Convocation on Immunology,* 261. H. Kohler et al., Eds., Longman Scientific and Technical, Harlon, Essex, Great Britain (1987). The relative importance of the secretory immune system becomes apparent when one realizes that 80% of the antibody-secreting cells in the body produce sIgA and that twice as much sIgA is secreted into the gastrointestinal tract than IgG is produced to enter the circulatory system each day, Brandtzaeg, P., in *Curr. Top. Microbiol. Immunol.* 146, 13 (1989).

The *Streptococcus mutans* group of microorganisms constitute the principal etiologic agents of dental caries. Gibbons, R. J. et al., *Ann. Rev. Med.* 26, 121 (1975); Hamada, S. et al., *Microbiol. Rev.* 44, 331 (1980). They colonize the tooth surface and remain there throughout life. Oral ingestion of killed *S. mutans* leads to the production of sIgA against *S. mutans* antigens in saliva, Michalek, S. M. et al., *Science* 191, 1238 (1976); Mastecky, J. et al., *J. Clin. Invest.* 61, 731 (1978) and this has been shown to be effective in preventing *S. mutans* colonization on the teeth of rodents and primates and thereby prevent induction of caries. Michalek et al., supra; Challacombe, S. J. et al., *Arch. Oral Biol.* 24, 917 (1980). Since sIgA must be present prior to colonization to be effective, individuals immunized to produce sIgA against *S. mutans* colonization antigens after colonization has occurred will continue to be colonized with *S. mutans* unless the bacteria are mechanically removed during dental propylaxis. Curtiss, R. III, in *Curr. Top. Microbiol. Immunol.* 118, 253 (1985). A diversity of techniques are used to determine which surface constituents of a pathogen are important for colonization and expression of virulence by that pathogen. Thus mutants can be isolated and tested for ability to colonize or cause disease. Gene cloning can be used to produce a gene product in a heterologous microorganism. The expressed gene product can be used to immunize animals to see whether colonization and/or virulence by the pathogen is inhibited. Based on such studies, scientists can infer relative importance to various colonization and virulence antigens and thereby choose those that are appropriate to use in vaccine compositions so as to immunize human or other animal hosts and prevent colonization and infection by the pathogen. Such studies have been performed with the *S. mutans* group of microorganisms to demonstrate the critical importance of the surface protein antigen A (SpaA; also known as antigen I/II, B, and P1), glucosyltransferases, dextranase and glucan-binding proteins. Curtiss, 1985 supra.

The surface protein antigen A (SpaA) constitutes a major protein antigen on the surface of *S. mutans*. Curtiss, R. III, et al., in *Streptococcal Genetics*, Ferretti, J. J. et al., Ed., American Society for Microbiology, Washington, D.C. pp. 212–216 (1987). The spaA gene has been cloned, Holt, R. G. et al., *Infect. Immun.* 38, 147 (1982), partially sequenced and the major antigenic determinants mapped. It is known that mice and humans intentionally or naturally immunized by oral ingestion of *S. mutans* produce sIgA in saliva against the SpaA protein. It is furthermore known that immunization of monkeys with antigen I/II (which is essentially immunologically identical to SpaA, Holt et al., supra) yields protective immunity against *S. mutans* colonization and *S. mutans*-induced dental caries, Russell, M. W. et al. *Immunol.* 40, 97 (1980).

Invasive *Salmonella*, such as *S. typhimurium* and *S. typhi* constitute the etiologic agents for typhoid fever in mice and humans, respectively. They gain access to deep tissues following oral ingestion by attaching to, invading, and proliferating in the GALT. Carter and Collins *J. Exp. Med.* 139, 1189 (1974). *Salmonella* can be rendered avirulent so as not to induce disease by introducing mutations in known genes. Germanier, R. et al., *Infect. Immun.* 4, 663 (1971); Germanier, R. et al., *J. Infect. Dis.* 131, 553 (1975); Hoiseth and Stocker, *Nature* 291, 238 (1981); Curtiss et al., *Infect. Immun.* 55, 3035 (1987). Such mutants are immunogenic when administered orally and retain their tissue tropism for the GALT. Curtiss, R. III, *J. Dent. Res.* 65, 1034 (1986); Curtiss, R. III et al., in *Proceedings of the Tenth International Convocation on Immunology*, 261. H. Kohler et al., Eds., Longman Scientific and Technical, Harlon, Essex, Great Britain (1987); Curtiss, R. III, et al., *Infect. Immun.* 55, 3035 (1987).

A number of *S. typhimurium* and *S. typhi* strains which possess various deletion mutations rendering them avirulent have been constructed with the ability to produce colonization and/or virulence antigens from several pathogens. Oral immunization leads to production of sIgA and IgG responses against the expressed antigen. Formal, S. B. et al., *Infect. Immun.* 34, 746 (1981); Stevenson, G. et al., *FEMS Microbiol. Lett.* 28, 317 (1985); Clements, J. D. et al., *Infect. Immun.* 53, 685 (1986); Maskell D. et al., in *Vaccines 86*, Cold Spring Harbor Laboratory, Cold Spring Harbor, N.Y., pp. 213–217 (1986). Recombinant avirulent *Salmonella* expressing the *S. mutans* SpaA and glucosyltransferase proteins have been constructed. Curtiss et al., in: *The Secretory Immune System*, J. R. McGhee and J. Mestecky, Eds., Ann. N.Y. Acad. Sci. 409, 688 (1983); Curtiss supra (1986); Curtiss et al., supra (1987); Curtiss et al., *Vaccine* 6, 155 (1988). Secretory antibodies (sIgA) against SpaA have been produced in saliva following oral immunization with avirulent *Salmonella* strains expressing the *S. mutans* SpaA protein, Curtiss, R. III et al., in *Mol. Microbiol. Immunol of Streptococcus mutans*, Hamada, S. et al., Eds., Elsevier, N.Y. pp. 173–180 (1986); Katz, J. et al., in *Recent Advances In Mucosal Immunology, Part B*, Mestecky, J. et al., Ed., Plenum Publishing Corp., pp. 1741–1747 (1987); Curtiss et al. 1987, supra.

SUMMARY OF THE INVENTION

The present invention is directed to transgenic plants which contain DNA sequences which code for a colonization antigen, a virulence antigen, antigenic determinants thereof or fusion proteins thereof of pathogenic microorganisms. The present invention is further directed to compositions useful for stimulating secretory immunity in humans and animals. The present invention is also directed to methods for making the compositions and producing transgenic plants and to methods for stimulating secretory immunity.

More specifically, the present invention is directed to transgenic plants which are capable of expressing a colonization antigen, a virulence antigen or antigenic determinants thereof of pathogenic microorganisms. The transgenic plants are useful for orally immunizing humans and animals to elicit a secretory immune response in the human or animals to inhibit colonization and/or invasion through a mucosal surface by said pathogenic microorganism.

The transgenic plants are produced by transforming plants with a plant transformation vector which contains at least one DNA sequence which codes for an antigen of a pathogenic microorganism. The antigen may be a colonizations antigen, a virulence antigen, an antigenic determinant of either antigen or a fusion protein containing either antigen or determinant. In addition to the antigen or antigenic determinant, the fusion protein may contain a polypeptide which stabilizes and/or enhances the activity of the antigen. The fusion protein may also be one or more antigens.

The plant transformation vectors are prepared by inserting one or more DNA sequences coding for the antigen of interest into a vector suitable for the transformation of plants. The vectors may be used for direct gene transfer or for agroinfection to insert the DNA sequences into the desired plants. The DNA sequences may be natural or synthetic and may comprise an entire gene or a fragment of a gene which codes for the antigen.

The compositions useful for eliciting a secretory immune response may be the transgenic plant itself or material derived from the plant. For example, the transgenic plant could be ingested directly by humans or animals or it could be processed to make a food product which is ingested by humans or animals. The compositions are useful for immunizing humans or animals against the pathogenic microorganisms to which the antigens correspond.

BRIEF DESCRIPTION OF THE FIGURES

FIGS. 6A–6C illustrates the construction of the plasmids pSUN339, pSUN340, pSUN341, pSUN342, pSUN343.

FIGS. 8A–8C depicts the entire 4,643 base pair nucleotide sequence of pSUN387.

Figure 1:
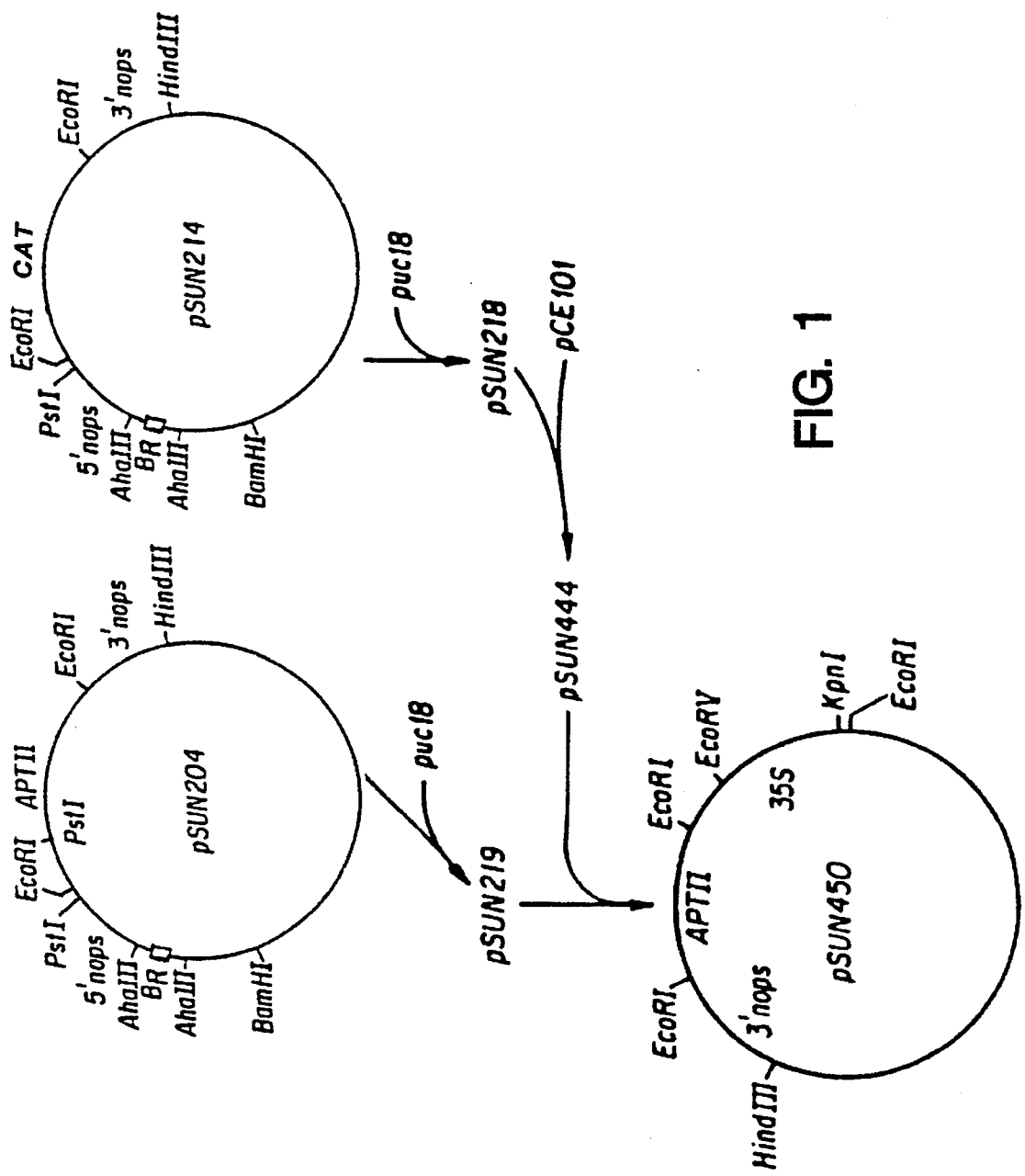
FIG. 1 illustrates the construction of the plasmid pSUN450.

Lane 1 contains pre-stained molecular weight standard.

Lane 2 contains 150 μg protein from a cell extract of tobacco not producing SpaA.

Lane 3 contains 150 μg protein from a cell extract of tobacco producing SpaA.

Lane 4 contains 150 μg protein from a cell extract of lyophilized tobacco which does not produce SpaA, and which was stored at −20° C. for 13 days.

Lane 5 contains 150 μg protein from a cell extract of lyophilized tobacco which produces SpaA, and which was stored at −20° C. for 13 days.

Lane 6 contains 150 μg protein from a cell extract of lyophilized tobacco which does not produce SpaA, and which was stored at room temperature for 13 days.

Lane 7 contains 150 μg protein from a cell extract of lyophilized tobacco which produces SpaA, and which was stored at room temperature for 13 days.

Lane 8 contains 300 -μg protein extract of 1:1 mixture of mouse meal to lyophilized tobacco which does not produce SpaA. The tobacco was stored at room temperature for 13 days.

Lane 9 contains 300 μg of protein extract of 1:1 mixture of mouse meal to lyophilized tobacco which produces SpaA. The tobacco was stored at room temperature for 13 days.

Lane 10 contains 150 μg protein extract of mouse meal.

DETAILED DESCRIPTION OF THE INVENTION

The present invention includes (a) plants, seeds, and plant tissue capable of expressing an antigen selected from the group of colonization and/or virulence antigens, and/or antigenic determinants thereof and/or fusion proteins of the antigens or determinants of pathogens; (b) compositions useful for the stimulation of a secretory immune response in a human or other animal; (c) methods for stimulating a secretory immune response in humans and other animals so as to inhibit colonization and/or invasion through mucosal surfaces by pathogens; (d) unique vectors containing DNA sequences coding for colonization or virulence antigens; and (e) a method of producing colonization or virulence antigens of pathogenic microorganisms in plants.

In order to provide a clear and consistent understanding of the specification and the claims, including the scope given to such terms, the following definitions are provided:

Antigen: A macromolecule which is capable of stimulating the production of antibodies upon introduction into a human or other animal. As used herein, antigen shall mean an antigen per se, an antigenic determinant of the antigen, or a fusion protein containing the antigen or antigenic determinant.

Antigenic Determinant: A small chemical complex that determines the specificity of an antigen-antibody reaction. Colonization and/or virulence antigens of a pathogen contain one or more antigenic determinants.

Colonization or Virulence Antigens: Antigens on the surface of a pathogenic microorganism that are associated with the ability of the microorganism to colonize or invade its host. Discussion and claims may refer to colonization or virulence antigens or antigenic determinants thereof. A pathogen may contain antigens of either colonization or virulence or both and one or more DNA sequences for each or both may be transferred to a vector and used to transform a plant such that it expresses the antigen or antigens.

Chimeric Sequence or Gene: A DNA sequence containing at least two heterologous parts, e.g., parts derived from, or having substantial sequence homology to, pre-existing DNA sequences which are not associated in their pre-existing states. The pre-existing DNA sequences may be of natural or synthetic origin.

Coding DNA Sequence: A DNA sequence from which the information for making a peptide molecule, mRNA or tRNA are transcribed. A DNA sequence may be a gene, combination of genes or a gene fragment.

Food: Food or foodstuff or feedstuff is a plant or any material obtained from a plant which is ingested by humans and other animals. This term is intended to include raw plant material which may be fed directly to humans and other animals or any processed plant material which is fed to humans and other animals. Materials obtained from a plant are intended to include any component of a plant which is eventually ingested by a human or other animal.

Foreign DNA: DNA which is exogenous to or not naturally found in the microorganism or plants to be transformed. Such foreign DNA includes viral, prokaryotic, and eukaryotic DNA, and may be naturally occurring DNA, chemically synthesized DNA, cDNA, mutated DNA or any combination of the same. The foreign DNA of the present invention is derived from or has substantial sequence homology to DNA of pathogenic microorganisms and viruses.

Gene: A discrete chromosomal region which is responsible for a discrete cellular product.

Microorganism: A member of one of the following classes: bacteria, fungi, protozoa or viruses.

Plant Tissue: Any tissue of a plant in plant or in culture. This term includes, but is not limited to, whole plants, plant cells, plant organs, plant seeds, protoplasts, callus, cell cultures and any group of plant cells organized into structural and/or functional units. The use of this term in conjunction with, or in the absence of, any specific type of plant tissue as listed above or otherwise embraced by this definition is not intended to be exclusive of any other type of plant tissue.

Plant Transformation Vector: A plasmid or viral vector that is capable of transforming plant tissue such that the plant tissue contains and expresses DNA not pre-existing in the plant tissues.

Pre-existing DNA Sequence: A DNA sequence that exists prior to its use, in toto or in part, in a product or method according to the present invention. While such pre-existence typically reflects a natural origin, pre-existing sequences may be of synthetic or other origin.

Secretory Immune Response: The formation and production of secretory IgA antibodies in secretions that bathe the mucosal surfaces of humans and other animals and in secretions from secretory glands. An agent which causes the formation and production of such antibodies is considered to stimulate secretory immunity or to elicit a secretory immune response. Secretory immunity is also sometimes referred to as mucosal immunity.

Substantial Sequence Homology: Substantial functional and/or structural equivalence between sequences of nucleotides or amino acids. Functional and/or structural differences between sequences having substantial sequence homology will be de minimus.

Transgenic Plant: A plant which contains and expresses DNA that was not pre-existing in the plant prior to the introduction of the DNA into the plant.

Colonization and/or Virulence Antigens of Escherichia coli

Effective immunity against the enterotoxic *E. coli* that colonize pigs calves, and humans can be achieved by including plant materials expressing the K88 pilus colonization antigen for the swine feed, K99 pilus colonization antigen for humans. Plant material containing the B subunit of the *E. coli* enterotoxin can be included in feed for humans, calves, and swine to serve as an adjuvant to enhance the immune response to the pilus colonization antigens but also to induce protective immunity against the enterotoxin which is produced by most enterotoxigenic strains of *E. coli* infecting swine, calves and humans. Since one could make a diversity of blends, it would be possible to immunize against a large number of pathogens at the same time. Continual feeding of the food, at the appropriate time, could be used not only to induce protective immunity in young animals but also for immunization of adult females of the species to permit transmission of effective immunity to the offspring either through eggs, by placental transfer, or in colostrum and milk.

Heat-Labile Toxin B Subunit

The nucleotide sequence of the gene for the heat-labile enterotoxin of *E. coli* has been determined. Yamamoto, T. and Yokota, T., *J. Bacteriol.* 155, 728 (1983). The EcoRI-HindIII DNA fragment containing the entire B subunit gene can be inserted into the plant transformation vector pSUN387 (see FIG. 7) by methods standard in the art and further modified using either oligonucleotide synthesis or the restriction enzymes NspbII or MaeI, which cleave the nucleotide sequence either seven amino acids or zero amino acids from the C-terminal end to permit insertion of a multiple cloning site to facilitate making a great diversity of fusion gene products leading to the production of fusion proteins with the heat-labile toxin B subunit (LT-B) as the N-terminus sequence.

It is thus possible to insert the LT-B sequence in a plant transformation vector and have it expressed in a suitable plant species. Induction of sIgA against LT-B will block uptake of the intact LT toxin and thereby decrease the severity of the diarrhea associated with enterotoxigenic *E. coli* infection. If the plant also produces K99 or K88 or one of the other pilus adhesive antigens, the induction of a sIgA response should also inhibit colonization by the enterotoxigenic *E. coli* and thus greatly diminish diarrhea.

E. coli Pap Pili genes

Pap pili genes of uropathogenic *E. coli* including genes for the pilus adhesin have been cloned, Lund, B., et al. *J. Bacteriol* 162, 1293 (1985) and have subsequently been sequenced. Uropathogenic *E. coli* may express several different pilus adhesins and cloned genes expressing several different pilus types are available, Clegg, S. *Infect Immun.* 38, 739 (1982); Van Die, I., et al. *FEMS Microbiol. Lett.* 19, 77 (1983); Normark, S., et al., *Infect. Immun.* 41, 942 (1983).

E. coli K99 Pilus Antigen

K99 pilus antigen is expressed by enterotoxigenic *E. coli* strains causing scours in calves. The gene for the K99 pilus antigen has been cloned and expressed, van Embden, J. D. A., et al. *Infect. Immun.* 29, 1125 (1980); deGraaf, F. K., et al. *Infect. Immun.* 43, 508 (1984) and sequenced, Roosendahl, E., et al., *FEMS Microbiol. Lett.* 22, 253 (1984). It is therefore straightforward to insert it into a plant transformation vector. Induction of sIgA against K99 pili blocks colonization in the calf intestine and thereby prevents scours.

E. coli K88 Pilus Antigen

K88 pilus antigen is expressed by enterotoxigenic *E. coli* strains causing severe diarrheal disease in pigs. The gene for the K88 pilus antigen necessary for intestinal colonization has been cloned, Mooi, F. R., EL et al., *Nuc. Acids Res.* 6, 849 (1979), Kehoe, M. et al., *J. Bacteriol.* 155, 1071 (1983) and sequenced, Gaastra, W., et al., *FEMS Microbiol. Lett.* 12, 41 (1981). It is therefore possible to insert this sequence into a plant transformation vector in such a way as to cause its synthesis in plants.

Genes for other pilus adhesions that permit colonization of enterotoxigenic and enteropathogenic *E. coli* in humans and in other animal hosts have been identified and in some cases cloned and sequenced, see Mooi, F. R. and deGraaf, F. K., *Curr. Top. Microbiol. Immunol.* 118, 119 (1985); Kaper, J. B. and M. M. Levine, Vaccine 6, 197 (1988).

Colonization and/or Virulence Antigens of Streptococcus mutans

Proteins associated with the surface of *S. mutans* include the surface protein antigen A (SpaA), glucosyltransferase B (GtfB), dextranase, glucosyltransferase C (GtfC), and glucan binding proteins.

*S. mutans* serotype g surface protein antigen A (SpaA)

The spaA gene from *S. mutans* serotype g strain UAB90 was cloned on a cosmid vector in *E. coli*. Holt, et al., 1983, Supra. The protein is essential for the initial colonization of the tooth surface and its absence precludes colonization of germfree rats (Curtiss, et al., 1987a supra; 1987b supra). The spaA gene has been subcloned, the major antigenic determinants of the protein determined and these regions of the gene sequenced.

S. mutans glucosyltransferase B

The *S. mutans* glucosyltransferase B is encoded by the gtfB gene and synthesizes water-insoluble glucan polymers and free fructose from sucrose. The gene has been cloned and sequenced by Shiroza, T. et al. *J. Bacteriol.* 169, 4263 (1987). The plasmid pSU20 (9.3 kb) contains a 6.5 kb PstI fragment encoding the 165,800 kilodalton (kDa) GtfB protein. Based on the known nucleotide sequence and the location of the ATG start codon, the coding sequence is inserted into a plant transformation vector using conventional techniques.

S. sobrinus (S. mutans serotype g) dextranase gene

The pYA902 cosmid clone expresses *S. sobrinus* dextranase, Barrett, J. F. et al., *Infect. Immun.* 55, 792 802 (1987), and Jacobs, W. R. et al., *Infect. Immun.* 52, 101 (1986). A partial PvuII digest of pYA902 DNA generated a series of plasmids with all or portions of the dextranase gene. pYA993 is a 5.45 kb plasmid expressing a slightly truncated dextranase of 110 kDa. A 2.6 kb PvuII fragment containing all of the dextranase coding sequence in pYA993 has been cloned in the correct orientation into the SmaI site of pUC8 by blunt-end ligation. This fragment has the dextranase ATG start codon but lacks the dextranase promotor. Thus it can readily be inserted into a plant transformation vector either to be directly expressed under the control of a plant promotor or as a tandem fusion construction fused to the C-terminal end of the spaA coding sequence, for example.

Plant Transformation Vectors

The vectors of the present invention are vectors which contain DNA coding for colonization and/or virulence antigens and are capable of transforming plants. Foreign DNA is DNA which is exogenous to or not naturally found in the organism to be transformed. It can be inserted into cloning vectors to transform plants. The foreign DNA of the present invention is derived from or has substantial sequence homology to DNA of pathogenic microorganisms and viruses. The vectors of the present invention are produced by standard techniques. However, the vector produced will depend on which type of transformation and which species of plant is being transformed. For example, if plant protoplasts are being transformed, the vector can be a Ti plasmid-derived vector or any vector which can be introduced by direct gene transfer means into the protoplasts. If a plant or plant organ or part thereof is being transformed, then the vector must be capable of transforming this type of tissue. In this instance, the novel plant transformation vector will likely be based on a Ti plasmid-derived vector, although vectors useful for microprojectile transformation can also be used. Appropriate vectors which can be utilized as starting materials are known in the art. Suitable vectors for transforming plant tissue have been described by deFramon, A. et al., *Bio/Technology* 1, 263 (1983); An, G. et al., *Embo J.* 4, 277 (1985); Potrykus, I. et al., supra; Rothstein S. J. et al., *Gene* 53, 153 (1987), as well as the other vectors described in the references discussed above. In addition to these vectors, many others have been produced in the art which are suitable for use in the present invention.

The construction of the vectors can be performed in a suitable host, for example, *E. coli*. Suitable *E. coli* strains include but are not limited to HB101, JM83, DH1, DH5α, LE392 and the like. If the vectors are used in a direct gene transfer or a micro-injection technique, they can be used directly. In certain instances it may be preferable to linearize the vector before use. If the vectors are to be used in an *A. tumefaciens* host, then the vector must first be transferred to the appropriate strain. This transfer is accomplished by conventional techniques, including biparental mating, Simon, R. et al., *Bio/Technology* 1, 74 (1983); triparental mating, Ditta, G. et al., *Proc. Natl. Acad. Sci.* USA 77, 7347 (1980) or transformation; Holsters, M. et al., *Mol. Gen. Genet.* 163, 181 (1978). Suitable strains of *A. tumefaciens* include but are not limited to LBA4404.

The vectors of the present invention contain DNA sequences encoding colonization or virulence antigens from a variety of pathogens known to cause diseases in humans and other animals. While the following description and many of the examples are directed to DNA sequences found naturally in pathogenic bacteria, this discussion applies equally to such sequences which occur and can be cloned from, viral, fungal and parasitic pathogens. Of course, DNA sequences derived by synthesis to encode colonization and/or virulence antigens or parts thereof, are similarly embraced.

A DNA sequence coding for a colonization or virulence antigen or a part of the antigen of a pathogen is obtained by conventional means and inserted into any vector suitable for the transformation of plants. For example, the DNA sequence can be isolated from a gene bank of genomic clones. Alternatively, the DNA sequence can be prepared by reverse transcription. The vectors are then introduced into plant cells by a variety of known techniques which give rise to transformed cells, tissues and plants.

The DNA sequence can be chemically synthesized if the amino acid sequence of the colonization or virulence antigen or part thereof is known. Several prior art methods can be utilized to determine the amino acid sequence of the colonization or virulence antigen. A part of the amino acid sequence can be determined and used to prepare a probe for reverse transcriptions.

The DNA sequence can contain a coding sequence for the specific amino acid sequence of the colonization or virulence antigen, or for one or more of its antigenic determinants. The DNA sequence can also contain additional coding sequences which code for all or part of a protein which contains the colonization or virulence antigen.

The DNA sequence encoding the colonization or virulence antigen or part thereof of a pathogenic microorganism is inserted into an appropriate vector in such a manner that the colonization or virulence antigen is correctly expressed. In other words, the DNA sequence is positioned in the proper orientation and reading frame so that the correct amino acid sequence is produced upon expression of the DNA sequence in plant tissue. In accordance with conventional techniques, a chimeric DNA sequence is generally constructed which contains a promoter operable in plant tissue and the DNA sequence coding for the colonization or virulence antigen. The chimeric DNA sequence may further contain 3' non-coding sequences operable in plant tissue. The chimeric DNA sequence may further contain a coding sequence for a polypeptide other than the protein containing the colonization or virulence antigen such that a fusion protein is produced upon expression. The chimeric DNA sequence can be prepared in situ within a suitable vector by inserting the DNA sequence coding for the colonization or virulence antigen into a restriction site of a known plant transformation vector. Alternatively, the chimeric gene could be first constructed and then inserted into a vector to produce a plant transformation vector.

A colonization or virulence antigen or part thereof can be modified to increase its resistance to proteolytic breakdown. To do this, it is possible to genetically engineer a fusion construct between a colonization or virulence antigen and a peptide that is completely resistant to intestinal proteases and which acts as an adjuvant of orally administered antigens. The LT-B subunit has both of these characteristics. Other peptides include the B subunit of choleratoxin (CT-B), PapG protein adhesin and the like discussed above. The fusion construct is prepared by conventional techniques.

Plant Transformation

The cells of plants are transformed with the vectors described above by any technique known in the art, including those described in the references discussed above and by techniques described in detail in the examples which follow. These techniques include but are not limited to direct infection or co-cultivation of plants or plant tissue with *A. tumefaciens*. A very suitable technique is the leaf disk transformation described by Horsch, R. B. et al., *Science* 225, 1229 (1985).

Alternatively, the vector can be transferred directly, for example by electroporation, by microinjection by microprojectiles or by transformation of protoplasts in the presence of polyethylene glycol (PEG), calcium chloride or in an electric field.

Following transformation, the transformed cell or plant tissue is selected or screened by conventional techniques. The transformed cell or plant tissue containing the chimeric DNA sequence discussed above is then regenerated by known procedures, including those described in the references discussed above and in the examples which follow for both monocot and dicot plants. The species which can be regenerated by these techniques include, but are not limited to, maize, sunflower, rapeseed, clover, tobacco, cotton, alfalfa, rice, potato, eggplant, cucumber and soybean. The regenerated plants are screened for transformation by standard methods. Progeny of the regenerated plants are screened and selected for the continued presence of the integrated DNA sequence in order to develop improved plant and seed lines. The DNA sequence can be moved into other genetic lines by a variety of techniques, including classical breeding, protoplast fusion, nuclear transfer and chromosome transfer.

Compositions for Inducing Immunity

The level of expression of an antigen can often be affected by the site of insertion into the vector. The quantity of a colonization or virulence antigen expressed in transgenic plants can be also optimized by retransformation with suitable vectors to increase the number of gene copies for the colonization and/or virulence antigen. Production of SpaA protein can be maximized by retransformation in at least three different ways. Vectors described above, constructs of vectors with enhanced promoter efficiency, or vectors carrying multiple copies of the spaA gene sequence or the sequence for a SpaA antigenic determinant can be inserted into plants already carrying spaA genetic material.

A large number of regenerated plants should be examined for production of colonization or virulence antigens. Those plants yielding the highest level of stable production of colonization or virulence antigens are selected. If the turnover rate of the colonization or virulence antigen is unacceptably high, the protein could be modified by a variety of procedures to enhance the stability of the protein in planta (i.e., removal or alteration of protease cleavage sites by site-directed mutagenesis of the DNA sequence encoding the antigen). The gene specifying the protein could be engineered so that the protein is introduced as a storage protein in seed and thereby ensure high levels of stable production. This would be most practical in soybean and cereal grains for example.

In order to be an effective immunogen a colonization or virulence antigen expressed by a plant must be sufficiently stable to withstand food processing and digestion.

The plant material may be fed directly to a human or other animal or processed into food by means that will not denature protein. For example, transgenic plants, such as alfalfa or maize, containing a desired colonization or virulence antigen could be fed directly to humans or to other animals such as cattle. If the colonization or virulence antigen was from a colonization factor of enteropathogenic or enterotoxigenic *E. coli*, secretory immunity to scours can be produced in the cattle. Similarly, the seeds, of a variety of transgenic plants expressing colonization or virulence factors of a pathogenic microorganism could be directly eaten by humans in order to elicit a secretory immune response against it.

Alternatively, the transgenic plant can be processed by conventional techniques to produce food for humans and other animals. For example, transgenic maize can be processed to produce cornmeal which can be fed to animals or used to prepare foods for humans.

It is conceivable in some instances that a colonization or virulence antigen might not be readily denaturable, therefore, in some cases, cooking of a foodstuff might not destroy immunogenicity. This is true with regard to the SpaA protein which retains its immunoreactivity after denaturation by boiling or by treatment with ionic detergents. On the other hand, other colonization antigens or virulence antigens might not be so resilient to denaturation. In some cases increased stability of the colonization or virulence antigen to denaturation can be achieved by fusing the antigen to a polypeptide that inhibits denaturation or fosters spontaneous renaturation under suitable conditions.

Stability of Colonization and Virulence Antigens

The quantity, stability and immunogenicity of a major colonization and/or virulence antigen of a pathogenic microorganism in transformed plants may be evaluated by means that are well known, particularly immunological means. These variables can be measured in transformed protoplasts and callus, and in the roots, stems, leaves and seeds of mature plants.

Colonization and/or virulence antigens specified by *S. mutans* or *E. coli* DNA in plant vectors and expressed in recombinant *E. coli* and other suitable microorganisms can be tested for stability after feeding. A culture of a microorganism which expresses a known colonization and/or virulence antigen is killed by known methods such as heat or radiation. It is then added to a known animal food such as commercially available mouse meal and subjected to food processing. Protein from the enhanced and processed mouse meal may be analyzed for quantity of the colonization and/or virulence antigen before feeding and at various stages of digestion after feeding. Analysis may be carried out by a variety of known methods including but not limited to western blot analysis following sodium dodecylsulfate (SDS) polyacrylamide gel electrophoresis, immunoprecipitation and enzyme linked immunosorbant assay (ELISA). The quantity of the antigen at various stages of digestion may be compared to the quantity before ingestion.

Immunological Response Following Oral Ingestion of Colonization and Virulence Antigens Immunogenicity of the antigen is analyzed as well. Recombinant *E. coli* expressing colonization and virulence antigens are evaluated for their ability upon feeding to elicit a secretory immune response which is dependent upon the ability of the colonization and the virulence antigens to survive through the intestinal tract without destruction of their immunogenicity by intestinal enzymes. Plant material enhanced with *S. mutans*, recombinant *E. coli* or other suitable microorganisms which have been killed by heat or radiation, is subject to food processing. It may then be stored dry or frozen. Transgenic plants are also processed and either fed to animals or mixed with animal feed and the immunogenicity is determined by quantitative sIgA against the colonization or virulence antigen in saliva or in intestinal washes using Enzyme Linked Immunosorbent assay (ELISA).

EXAMPLES

Recombinant DNA Methods Used In The Examples Below

DNA manipulations were carried out using enzymes in accordance with the manufacturers' recommended procedures unless indicated otherwise. All enzymes were obtained from New England BioLabs or Bethesda Research Laboratories (BRL). All vector constructions were carried out in *E. coli* DH1, JM83 or DH5α unless indicated otherwise. The vectors were introduced into strains of *E. coli* different from the construction strains using conventional techniques. DNA isolations and *E. coli* transformations were conducted in accordance with Hanahan et al., *J. Mol. Biol.* 166, 557 (1983). Blunt-end ligations in 15% polyethylene glycol (PEG) were performed in accordance with Livak, *Anal. Biochem.* 152, 66 (1986). Additional techniques are described in Maniantis, T. et al., *Molecular Cloning, A Laboratory Manual*, 2nd Ed., Cold Spring Harbor Laboratory, Cold Spring Harbor, N.Y. (1988), *Methods in Enzymology* Vol 68 (1979), Vol 100 (1983), Vol 101 (1983), Vol 118 (1986) and Vol 152–154 (1987); and *Plant Molecular Biology: Manual*, Gelvin, SB and Schilperoort, RA, eds., Kluwer Academic Publishers, Dodrecht (1988).

EXAMPLE 1

I. Vector Constructions

Vectors useful for expressibly transforming plants with DNA sequences encoding colonization or virulence antigens are pSUN341 and pSUN343. Extensive information has been included in example 1 in order to enable the construction of these vectors from starting materials that are widely known and generally available. The extensive information available herein will enable the construction of similar vectors from other starting material.

A. Construction of Plasmid Vectors pSUN341 and pSUN343

1. Construction of pSUN450

The plasmid pSUN214 (ATCC 67470) was digested with PstI and HindIII. The 1.6 kb fragment was isolated containing the gene for chloramphenicol acetyl transferase (CAT) and the 3'-NOPS (nopaline synthase) sequence to provide a site for PolyA addition required for eukaryotic gene expression. The plasmid pUC18 was digested with PstI and HindIII and ligated with the isolated fragment. The resulting plasmid pSUN218 was isolated.

The plasmid pSUN218 was digested with SmaI and treated with calf intestinal alkaline phosphatase. The plasmid pCE101, Guilley, H. et al., *Cell* 30, 763 (1982), was obtained from K. Richards and digested with HphI. The fragment containing the 35S promoter of cauliflower mosaic virus, a sequence which permits transcription in plant cells was isolated and treated with T4 DNA polymerase. This fragment was blunt-end ligated in 15% PEG to the treated pSUN218 to produce the plasmid pSUN444.

The plasmid pSUN204 (ATCC 67469) was digested with HindIII and then partially digested with PstI. The larger 1.6 kb APTII-3'-NOPS containing fragment was isolated. The APTII gene confers resistance to the antibiotics kanamycin, neomycin and G418 and as such provides a useful transformation, selection determinant inplants. The plasmid pUC18 was digested with PstI and HindIII and ligated to the APT II-3'-NOPS fragment. The resulting plasmid was identified as pSUN219.

The plasmid pSUN219 was digested with SalI and treated with the Klenow fragment of DNA polymerase I. The DNA was then digested with HINDIII and the fragment containing the APT II-3'-NOPS sequences was isolated. The plasmid pSUN444 was digested with BamHI and treated with the Klenow fragment of DNA polymerase I. The treated vector was then digested with HindIII. The 3.5 kb large fragment was isolated and ligated to the APT II-3'-NOPS containing fragment from pSUN219. The resulting plasmid was identified as pSUN450. The construction and partial map of pSUN450 are illustrated in FIG. 1.

2. Construction of pSUN470

The plasmid pSUN450 was digested with HindIII and treated with the Klenow fragment of DNA polymerase I. The treated vector was then digested with KpnI, and the 2.5 kb fragment containing the 35S promoter, APT II and 3'-NOPS sequences was isolated. The plasmid pGA470 (obtained from G. An) was digested with SalI and EcoRI. A 500 bp fragment containing the left border ($B_L$) sequence was isolated and ligated into the EcoRI site of pUC18. The vector pSUN402 was identified and isolated.

Figure 2:
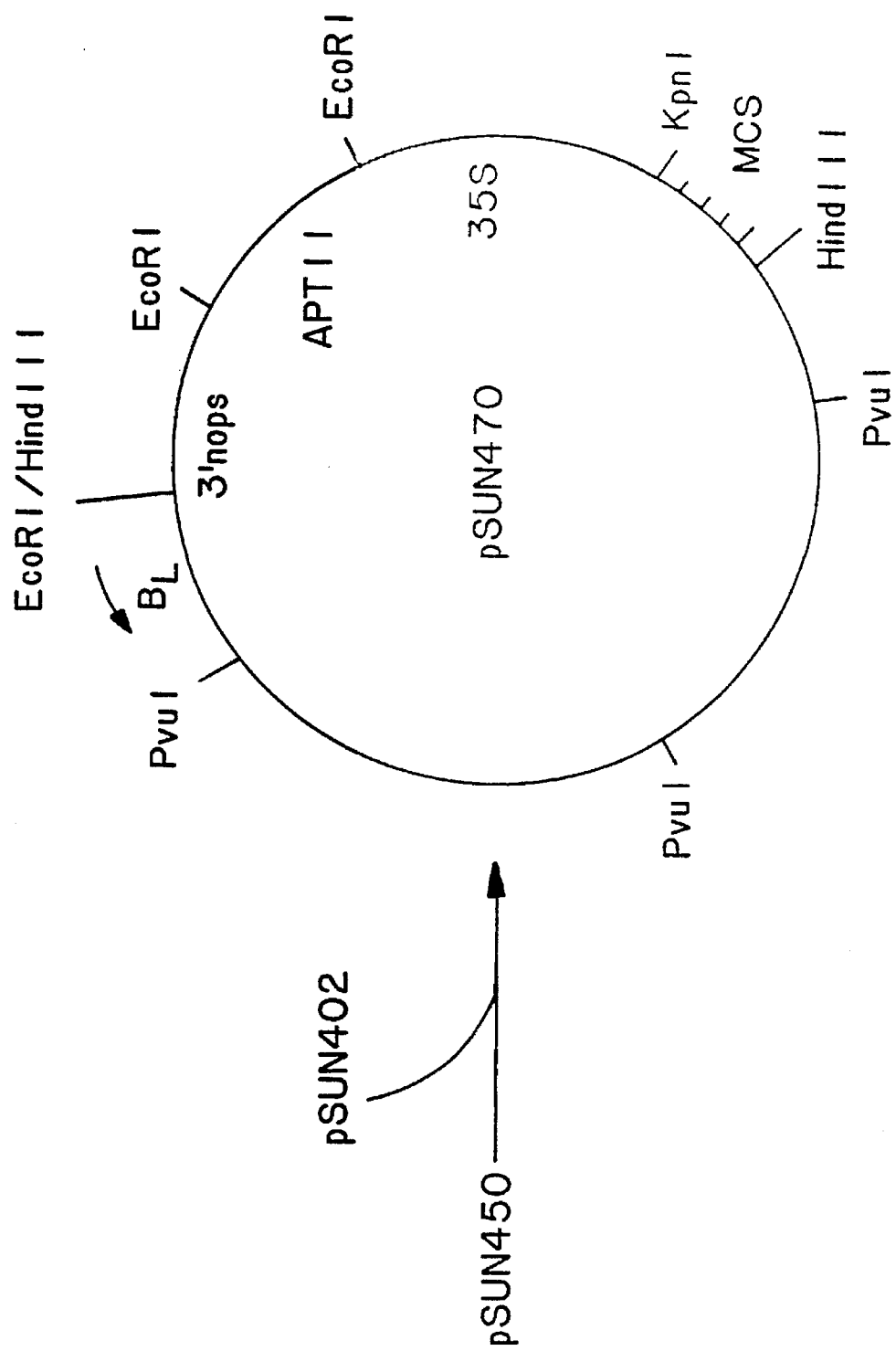
FIG. 2 illustrates the construction of the plasmid pSUN470.

The plasmid pSUN402 was digested with EcoRI and treated with the Klenow fragment of DNA polymerase I. The treated vector was then digested with KpnI and ligated to the fragment isolated from pSUN450. The plasmid pSUN470 was identified. The construction and partial map of pSUN470 are illustrated in FIG. 2. pSUN470 contains the multiple cloning site (MCS) of pUC18 including restriction sites from KpnI through HindIII.

3. Construction of pSUN221

Figure 3:
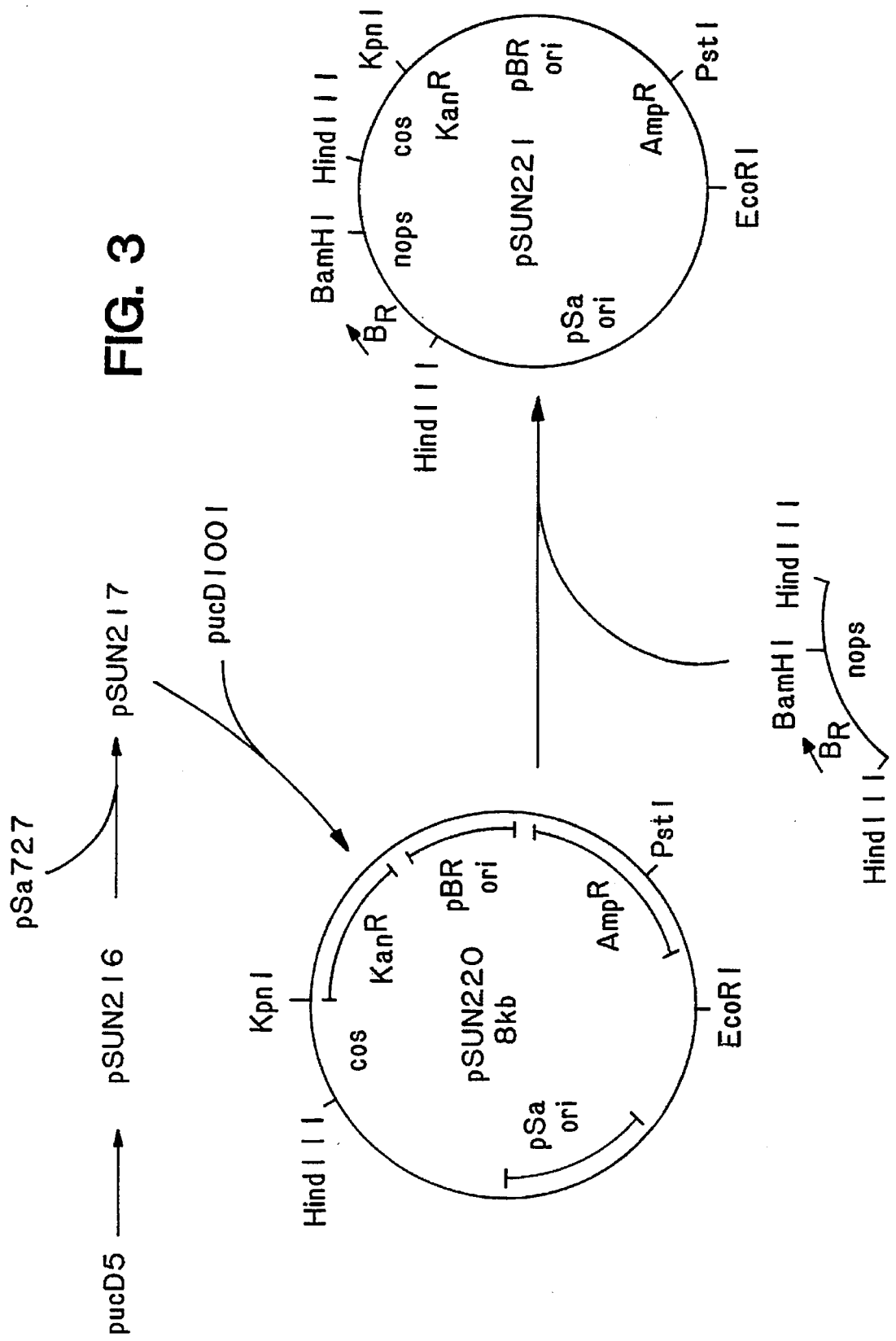
FIG. 3 illustrates the construction of the plasmid pSUN221.

The plasmid pSUN220 (ATCC67471) containing the origin of replication (ori) of the plasmid pBR322, for amplifiable replication in *E. coli* and that of the broad host range plasmid pSa727 which permits replication in *Agrobacterium* (Tait, R. C. et al., *Biotech* 1, 269) (1982), as well as the sequence comprising the cohesive end termini (COS) of the bacteriophage lambda, was digested with HindIII and treated with calf intestinal alkaline phosphatase. HindIII fragment No. 23 (H23) containing the T-DNA right border and the nopaline synthase gene from the *Agrobacterium* plasmid pTi337, Bevan, M. et al., supra, was isolated following HindIII digestion of MWB2341:H23 (obtained from W. Barnes). The H23 fragment was ligated to the HindIII-digested plasmid pSUN220 to produce the plasmid pSUN221. The construction of pSUN221 is shown in FIG. 3.

4. Construction of pSUN473

Figure 4:
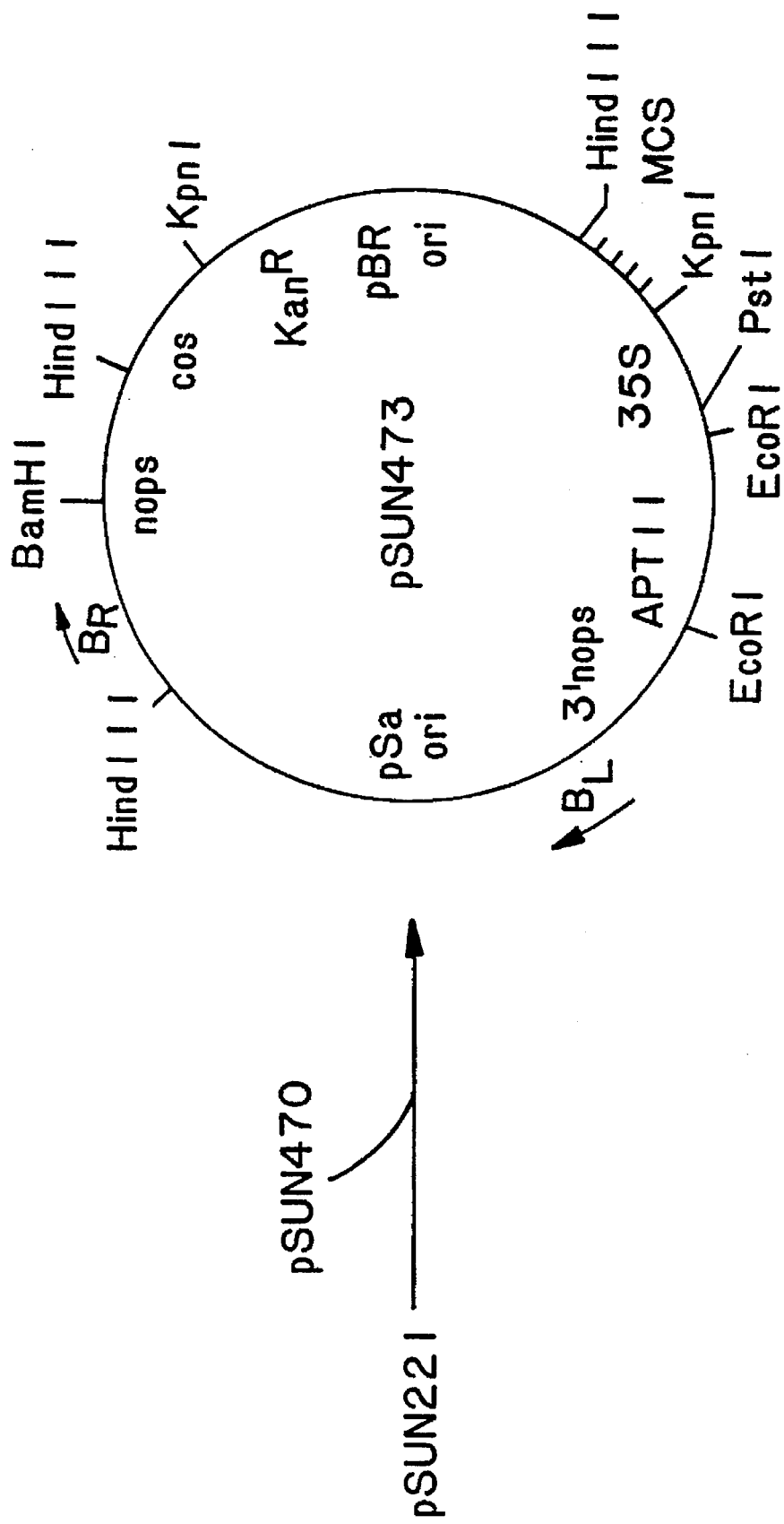
FIG. 4 illustrates the construction of the plasmid pSUN473.

The plasmid pSUN221 was digested with PstI and EcoRI and treated with mung bean nuclease. The plasmid pSUN470 was digested with PvuI and treated with mung bean nuclease. The 3.1 kb PvuI fragment containing the 35S promoter, APT II, 3'NOPS and $B_L$ sequences was isolated and blunt-end ligated in 15% PEG to the treated pSUN221. The ampicillin resistance determinant of pSUN221 ($Amp^R$) was destroyed in the process. The resulting plasmid was identified as pSUN473. The construction and partial map of pSUN473 are illustrated in FIG. 4. pSUN473, because of the pSa origin of replication, can be maintained in *A. tumefaciens* and is suitable for use as a binary vector for transfer of genetically engineered T-DNA sequences to plants.

5. Construction of pSUN474

The plasmid pSV2-hph was obtained from C. Kado, University of California, Davis, Calif., as a source of a gene which confers resistance to the antibiotic hygromycin (hph) useful as a transformation selection determinant in plants. pSV2-hph was digested with HINDIII and BglII and a 1.4 kb fragment containing the hph gene was isolated and purified.

The plasmid pBSM was obtained from Vector Cloning Systems, now known as Strategene Cloning Systems, La Jolla, Calif. and digested with HindIII and BamHI followed by treatment with calf intestinal alkaline phosphatase. The 1.4 kb hph-fragment from pSV2-hph was then ligated to the digested pBSM to produce pSUN474.

6. Construction of pSUN475

The plasmid pSUN474 was digested with HindIII and AvaI and the "sticky ends" of the DNA fragments produced by this digestion were made blunt by treatment with the Klenow fragment of E. coli DNA PolI in the presence of dNTP's. A 1.3 kb fragment containing the hph gene was isolated and purified.

Figure 5:
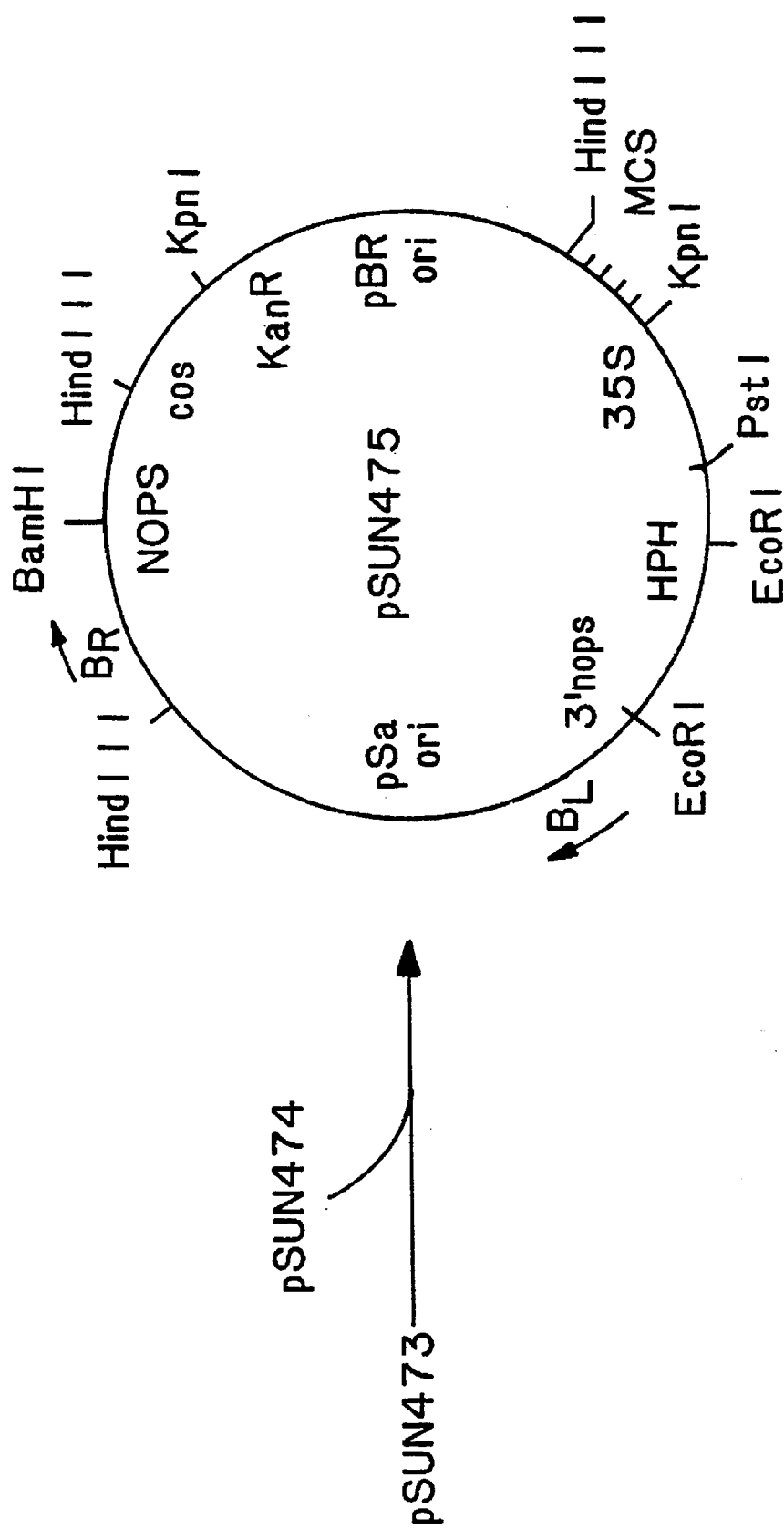
FIG. 5 illustrates the construction of the plasmid pSUN475.

The plasmid pSUN473 was digested with EcoRI, treated with the Klenow fragment of E. coli DNA PolI in the presence of DNYP's followed by treatment with calf intestinal alkaline phosphatase. A fragment of approximately 13 kb was isolated and purified. This 13 kb fragment and the 1.3 kb hph-fragment were blunt end ligated in the presence of 15% PEG to produce pSUN475. The filled-in EcoRI end of pSUN473 when ligated to the filled-in AvaI end of the hph-fragment regenerated an EcoRI site. The construction and partial map of pSUN475 are illustrated in FIG. 5.

7. Construction of pSUN480

The plasmid pSUN214 (ATCC 67470) (see FIG. 1) was digested with BamHI followed by treatment with the Klenow fragment of E. coli DNA PolI in the presence of dNTP's to fill in the ends. Further digestion with EcoRI followed by treatment with calf intestinal alkaline phosphatase permitted the isolation and purification of a 3.4 kb fragment containing the 3'NOPS sequence and the pUC origin of replication and ampicillin resistance determinant sequences found in pSUN214.

Figure 6B:
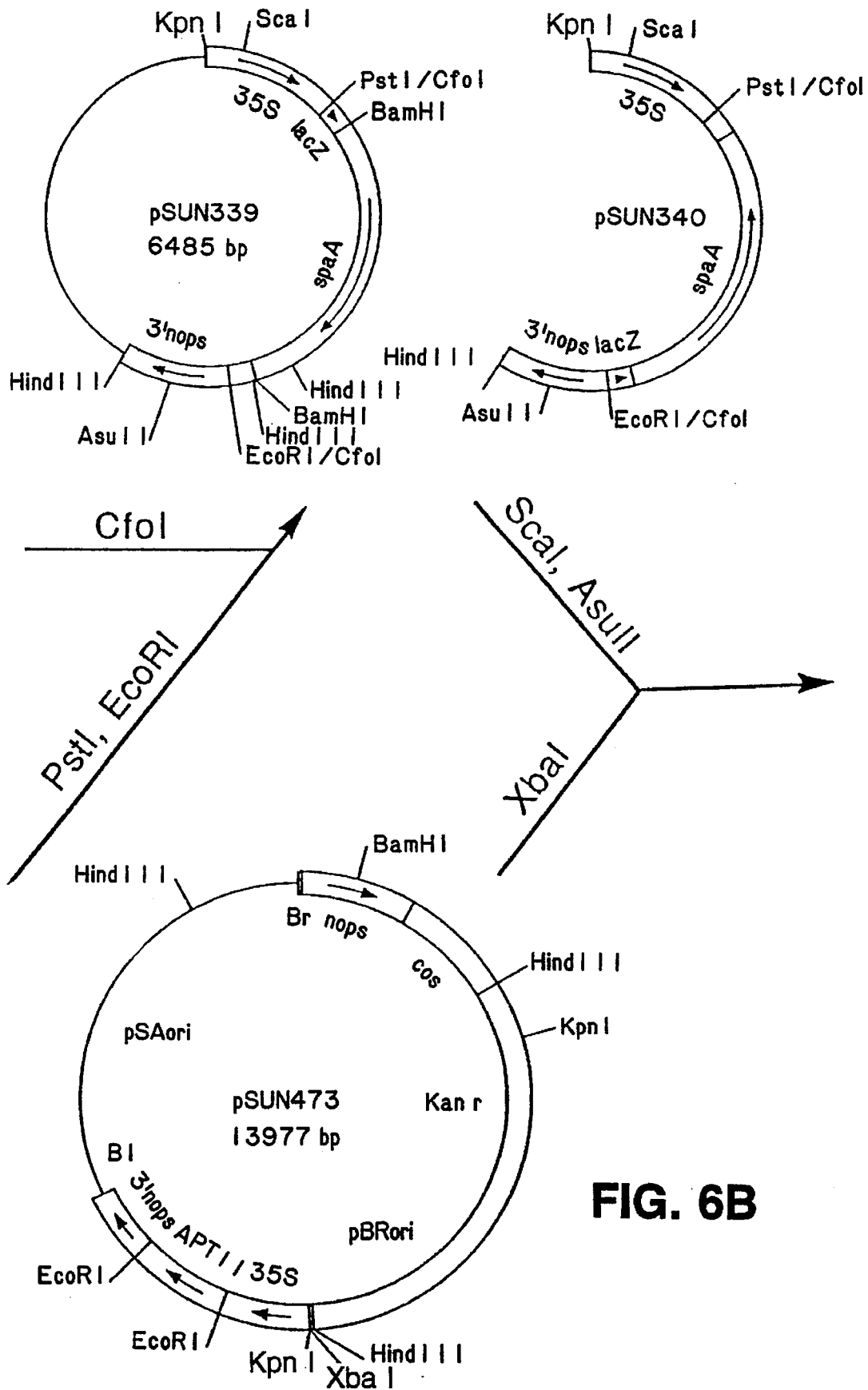
Figure 6C:
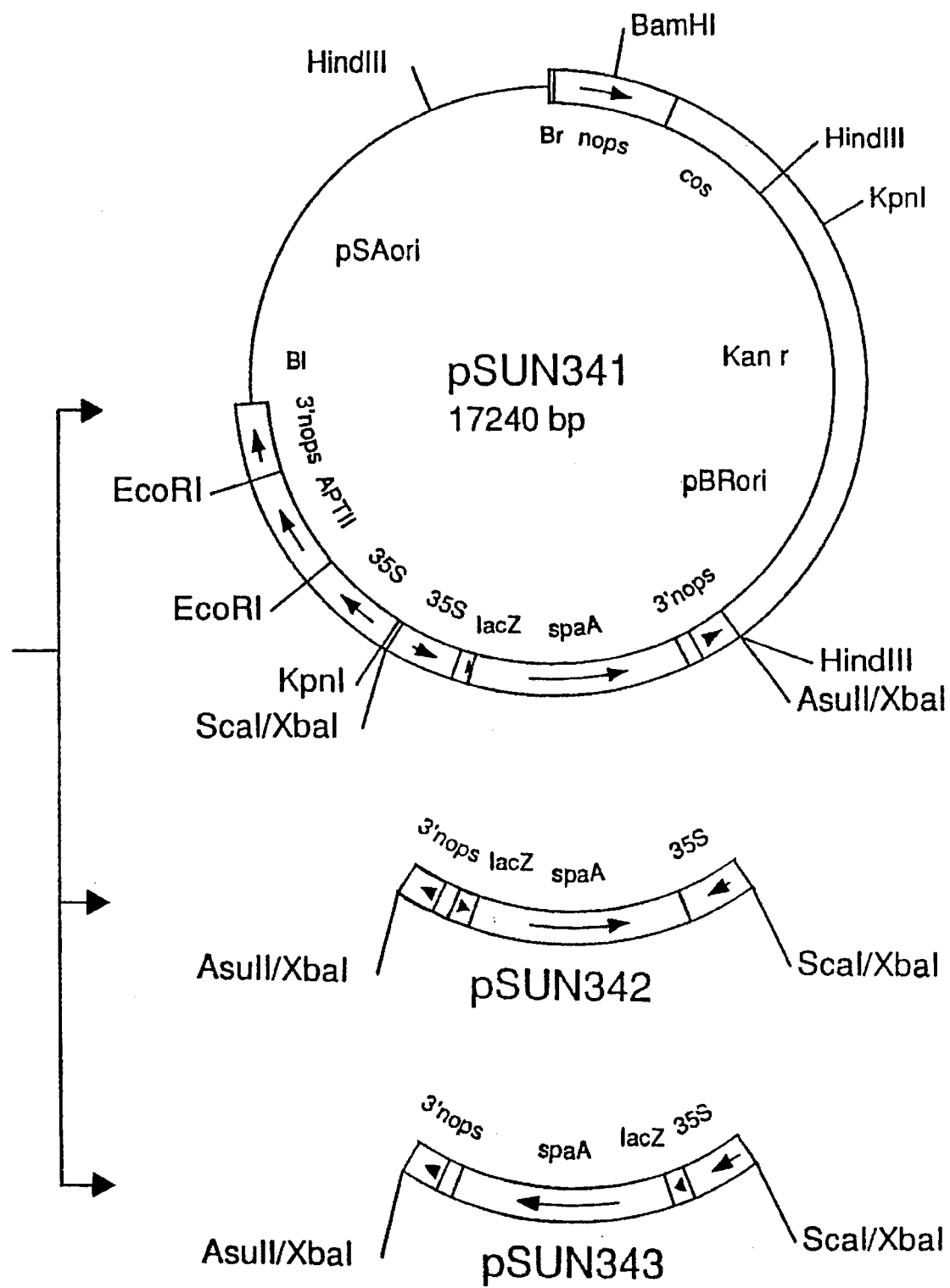

The plasmid pSUN475 was digested with XbaI (which cuts in the multiple cloning site MCS) followed by treatment with the Klenow fragment of E. coli DNA PolI in the presence of dNTP's to fill in the ends. The resulting linearized pSUN475 was then partially digested with EcoRI and a 2.15 kb fragment containing the CaMV 35S promoter and the hph coding sequence was isolated and purified. This fragment was ligated to the 3.4 kb fragment from pSUN214 and the resulting plasmid was pSUN480 which is depicted in FIG. 6.

8. Construction of pSUN339 and pSUN340

The plasmid pYA208 (see FIG. 6) was digested with CfoI and treated with $T_4$ polymerase in the presence of dNTP's to generate blunt ends. A fragment of about 2280 base pairs containing an expressible lac fusion to the spaA sequence was isolated. Plasmid pYA208 contains a BamHI fragment containing the spaA gene in the correct orientation. The vector pSUN480 was digested with PstI and EcoRI to remove the hygromycin resistance gene, and treated with T4 DNA polymerase and dNTP's to generate blunt ends. The larger fragment of 4170 base pairs was isolated. The lac-spaA fragment was ligated between the 35S and 3'NOPS sequences in the correct orientation in place of the hph-fragment to produce the plasmid pSUN339. pSUN340 which has the lacZ-spaA insert in the opposite orientation relative to the vector sequence was also isolated. (See FIG. 6).

9. Construction of pSUN341, pSUN342 and pSUN343

The plasmid pSUN339 was digested with ScaI and AsuII and the 35S-lacZ-spaA-3'NOPS fragment of about 3263 base pairs was isolated. The AsuII terminus of the fragment was filled in with dNTP's using the Klenow fragment of E. coli DNA polI.

The plasmid pSUN473 (FIG. 4) was digested with XbaI, which has a single site in the multiple cloning site sequence and the 5'end was filled in with dNTP's using the Klenow fragment of E. coli DNA polymerase I. The 35S-lacZ-spaA-3'NOPS expression cassette from pSUN339 was ligated to the digested plasmid pSUN473 in different orientations with regard to the 35S-APTII-3'NOPS sequence of the vector. The plasmid pSUN341 contains these sets of sequences in a head to head orientation. The plasmid pSUN343 contains these sets of sequences in a head to tail orientation. Plasmid pSUN342 was constructed in a similar fashion using pSUN340 as the starting material for Sca-I-AsuII digestion. The plasmids pSUN344 and pSUN345 are independent isolates identical to pSUN343. The plasmid pSUN346 is an independent isolate identical to pSUN341. The constructions of pSUN341, pSUN342 and pSUN343 are illustrated in FIG. 6. pSUN341 and pSUN343 have opposite orientations of the insert relative to the vector but with the CaMV 35S and lac promoters in the same correct orientations to permit SpaA expression in both E. coli and plants. pSUN341 in E. coli DH5α and pSUN343 in E. coli DH5α were deposited at the ATCC under the Budapest Treaty on Aug. 31, 1988 and assigned the numbers 67,787 and 67,785, respectively. pSUN342 was constructed as a control using the ScaI to AsuII fragment of pSUN340 into XbaI cut pSUN473. In this construct SpaA should be synthesized in E. coli under the control of the lac promoter but not in plants since the CaMV 35S promoter is in the wrong orientation (see FIG. 6).

B. Construction of pSUN387

The plasmid pSUN387 contains components of the plasmids pUC18, pSUN335 and pSUN491. pSUN491 (ATCC No. 67786) is deposited under the Budapest Treaty. The pUC component includes all sequences outside of the EcoRI and HindIII sites of the multiple cloning region. This contains the origin of replication and the gene for ampicillin resistance. The sequences from pSUN491 include the CaMV 35S promoter with a tandem duplication of a 327 bp HincII to EcoRV fragment which contains sequences shown to confer transcriptional enhancement to the 35S promoter and other heterologous promoters in plant systems. Kay et al., *Science* 236, 1299 (1987). Also, a multiple cloning region containing sites for NcoI, BamHI, XbaI, SalI, PstI and EcoRI followed by about 681 base pairs of 3'NOPS sequence are included downstream of the 35S promoter. The plasmid pSUN335 provides two sequences to permit the expression of genes in bacteria when inserted between the 35S promoter and 3'NOPS. These include a synthetic 17 bp KpnI to NcoI fragment which contains a perfect Shine—Dalgarno sequence, optimally spaced from the ATG contained within the NcoI site required for initiation of protein synthesis. Shine and Dalgarno, *Proc. Natl. Acad. Sci.* USA 71, 1342 (1974). Also included, upstream of the 35S promoter, is the promoter from the asd gene of *Streptoccus mutans* which has been shown to be a strong promoter of transcription in *E. coli*. Cardineau and Curtiss, *J. Biol. Chem.* 262, 3344 (1987).

Figure 7:
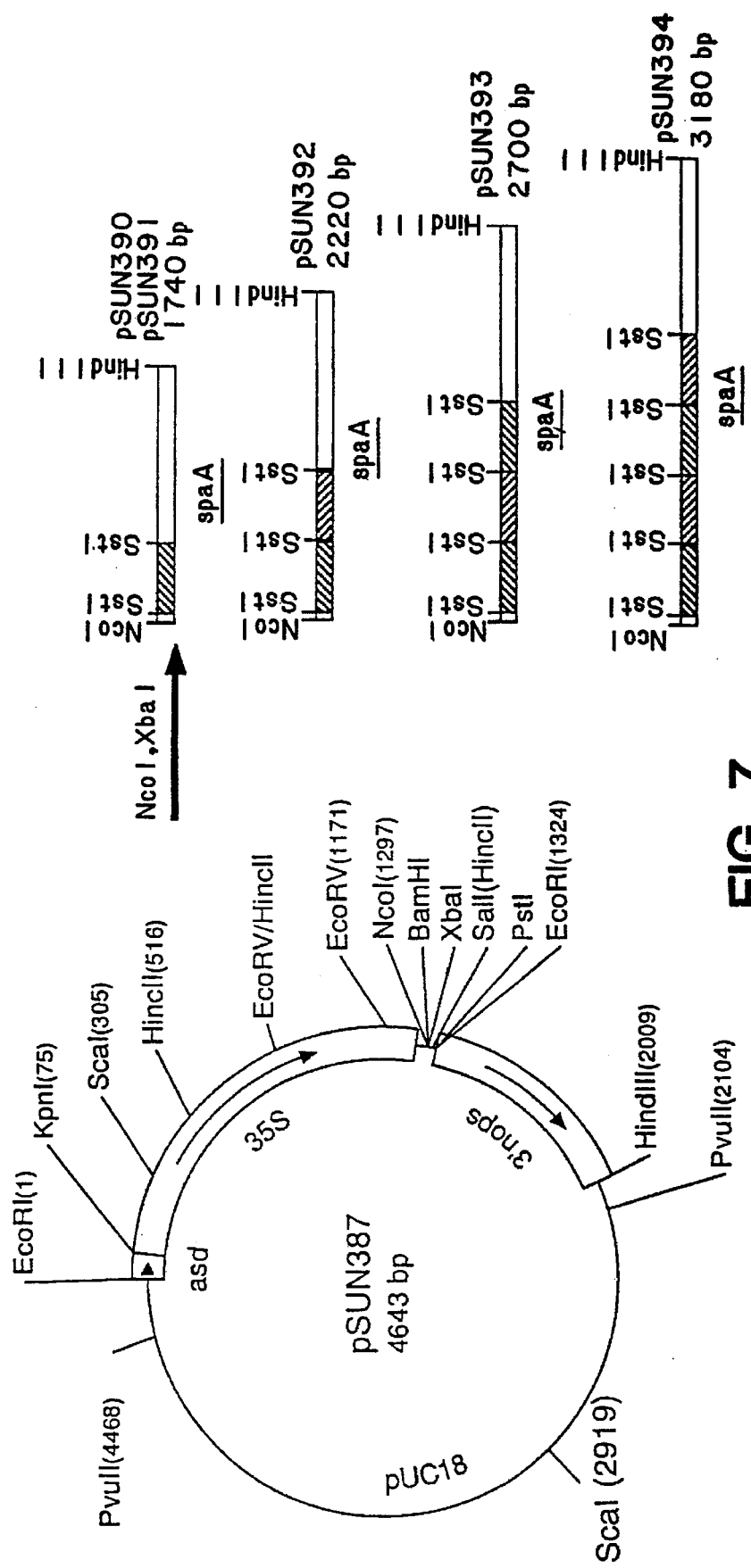
FIG. 7 illustrates the construction of the plasmids pSUN387, pSUN390, pSUN391 pSUN392, pSUN393 and pSUN394.

A map of pSUN387 is seen in FIG. 7. The sequence of the plasmid is also provided in FIG. 8. pSUN387 is deposited under the Budapest Treaty and is assigned ATCC No.

C. Construction of pSUN390, pSUN391, pSUN392, pSUN393 and pSUN394

The plasmids pYA177, pYA178, pYA179 and pYA180 (Curtiss et al., Vaccine 1988, supra) possess 1, 2, 3 or 4 copies of a 483 base pair SstI to SstI fragment, respectively, specifying the major antigenic/immunogenic determinant of the SpaA protein followed by a C terminal antigenic/ immunogenic determinant of the SpaA protein specified by approximately 1204 base pairs. Cloning was accomplished by digesting pSUN387 with XbaI which cuts the multiple cloning site, generating blunt ends using the Klenow fragment of DNA polymerase 1 and then digested with NcoI. The fragments specifying SpaA determinants were cut out of pYA177, pYA178, pYA179 and pYA180 by first digesting with HindIII, treating with Klenow and then cutting with NcoI after which the fragments were ligated into the prepared pSUN387 DNA.

As revealed by analysis of the complete nucleotide sequence of pSUN387 (see FIG. 8), expression of SpaA in E. coli is under the control of the S. mutans asd promoter and in plants under the control of the CaMV 35S promoter. In this construct, there are no ATG start codons following the CaMV 35S promoter prior to the ATG start codon at the NcoI site which initiates the reading frame for all of the SpaA inserts in pSUN390, pSUN391, pSUN392, pSUN393 and pSUN394. E. coli HB101 (pYA726) with a SpaA insert is deposited under ATCC No. 31985. This deposit is made available to the public by declaration in allowed U.S. application No. 773,894.

II. Expression and Stability of SpaA Protein

Figure 9:
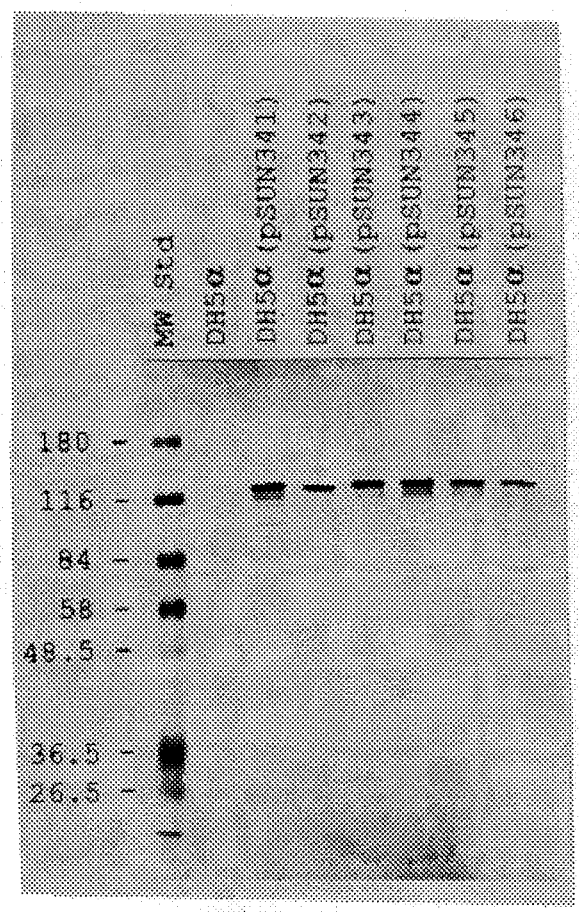
FIG. 9 illustrates the results of a Western blot analysis of SpaA protein synthesis detected by rabbit anti-SpaA sera in *E. coli* DH5α (lane 2) and in *E. coli* DHα containing plasmids pSUN341 (lane 3), pSUN342 (lane 4), pSUN343 (lane 5), pSUN344 (similar or identical to pSUN343; lane 6) pSUN345 (similar or identical to pSUN343; lane 7) and pSUN346 (similar or identical to pSUN341; lane 8). Prestained molecular weight markers are included in lane 1.

FIG. 9 shows a Western blot analysis of transformed E. coli DH5α expressing the SpaA protein due to the presence of pSUN341, pSUN342, pSUN343, pSUN344, pSUN345 and pSUN346. SpaA occurs at about 116 kDa. Expression of SpaA in E. coli is independent of the orientation of the CaMV promoter but is dependent on the correct orientation of the lac promoter. SpaA breakdown products occur primarily in the region from about 60 kDa to about 115 kDa. It is apparent from this analysis that antibody against SpaA recognizes all forms of the protein, native as well as breakdown products. This is advantageous since breakdown products could occur in planta as well as in the intestine.

Figure 10:
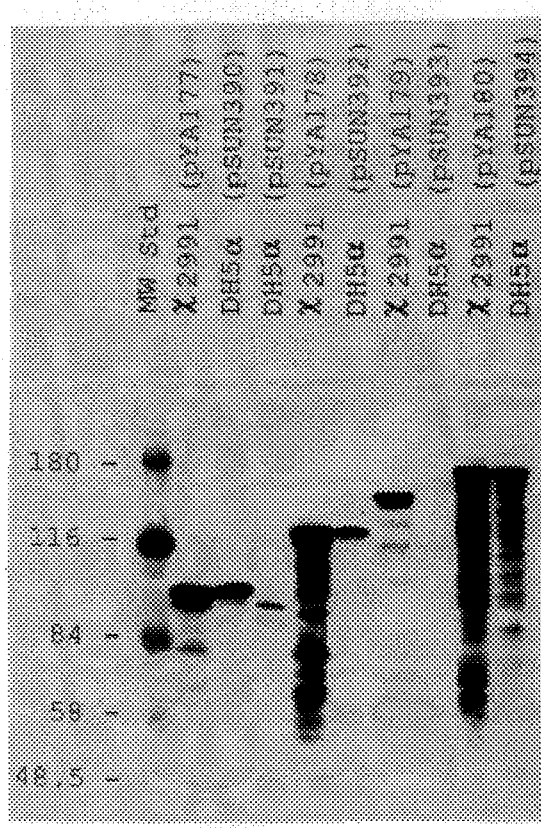
FIG. 10 illustrates the results of a Western blot analysis of SpaA protein synthesis as revealed by reaction with rabbit anti-SpaA sera in *E. coli* χ2991 containing pYA177, pYA178, pYA179 and pYA180 and in *E. coli* DH5α containing pSUN390, pSUN391, pSUN392, pSUN393, and pSUN394. Lane 1 contains prestained molecular weight standards.

FIG. 10 shows a Western blot analysis of SpaA protein synthesis by E. coli containing recombinant plasmids specifying SpaA antigenic/immunogenic determinants. The recombinant plasmids pYA177–pYA180 are contained in E. coli χ2991 whereas all of the pSUN390–pSUN394 recombinant vectors are contained in E. coli DH5α. pSUN390 and pSUN391 each specify one of two major bands specified by pYA177. The reason for this is not known. It is apparent that pSUN393 is not behaving in an expected way with regard to production of SpaA. Upon initial isolation it caused a much higher level of SpaA synthesis. All of the pSUN plasmid constructs cause synthesis of less SpaA than the pYA constructs. This is most likely because the S. mutans asd promoter is some 1250 base pairs away from the ATG start codon for SpaA synthesis in the pSUN vectors whereas the distance between the trc promotor and the ATG start in the pYA vectors is only 45 base pairs. The SpaA polypeptides specified by pYA177, pYA178, pYA179, and pYA180 had molecular masses of 94, 116, 145 and 164 kDa, respectively. Again SpaA breakdown occurs in E. coli but these breakdown products are recognized by the antibodies against the SpaA native protein.

Prior to conducting studies to see whether E. coli expressing SpaA could elicit an immune response after oral feeding to mice, studies were undertaken to investigate the stability of SpaA protein expressed in E. coli to various food processing regimens. In general, heating of E. coli χ2846 possessing pYA210 (a recombinant vector similar to pYA208 depicted in FIG. 6 but containing three tandem repeats, all in the same reading frame, of the 2.0 kb BamHI fragment in pYA208 specifying SpaA) to temperatures of 80° C. or above for 10 minutes or more completely stabilized SpaA from breakdown during storage at room temperature or in the cold. Attempts to examine the stability of purified SpaA protein or of SpaA protein released by lysed cells of E. coli χ2846 containing pYA210 when mixed with mouse meal were hampered by the fact that constituents in mouse meal interfered with SDS gel electrophoresis and Western blot analysis. It was thus not possible to accurately quantitate stability of SpaA antigenicity in mouse meal either before or after ingestion. Nevertheless, immunogenicity is an excellent indicator of stability during food processing and digestion since the antigen must survive to arrive in the small intestine to be taken up by M cells overlying the gut-associated lymphoid tissue.

III. Immunogenicity of SpaA Protein

Plant material containing heat-killed and lysed E. coli χ2846/pYA210 was lyophilized and ground to a meal. It was then stored in the dry state. Based upon analyses of quantity of SpaA protein relative to total protein, as described above, mouse meal was prepared so as to have 25 to 500 nanograms of SpaA protein per gram of meal. This diet was fed ad libitum to female BALB/c mice, 9 to 10 weeks old. The mice were weighed weekly to follow their growth and development. Mice were observed visually to determine the status of their health.

Saliva samples were collected weekly. Salivation was stimulated by pilocarpine. Serum was collected biweekly using retroorbital bleeding.

Serum anti-SpaA IgG and salivary IgA were detected by ELISA. Dynatech Laboratories immulon-1 flat-bottom polystyrene plates were coated overnight at 41° C. with 100 µl (4.25 µg protein) of a 1:5 dilution (in 0.1M NaHCO₃ buffer, pH 9.6) of semi-purified SpaA (obtained from a 70% ammonium sulfate precipitated filtered supernatant fluid from S. mutans followed by dialysis and lyophilization) or of SpaA purified from recombinant E. coli. Plates were then washed three times with phosphate buffered saline (PBS; pH 7.2) containing 0.05% Tween-20 and then blocked for 90 min. with PBS plus 0.05% Tween-20 and 1% bovine serum albumin. After washing, serum samples (100 µl of each dilution) were added and allowed to incubate overnight at 4° C. Plates were washed again and the secondary antibodies which were affinity purified goat anti-mouse IgG (chain specific) or goat anti-mouse IgA (γ-chain specific) conjugated with alkaline phosphatase (1:1000 dilution) added and incubated for 4 hours at room temperature. After washing, nitrophenyl phosphate substrate dissolved in diethylalamine buffer, pH 9.8, was added and plates incubated at room temperature for 1.5 hours. They were then read at 405 nm, with a Bio-Tek Automated EIA Plate Reader. Standardization of anti-SpaA serum IgG and serum IgA in comparison to total serum IgA and IgG were accomplished by use of purified mouse IgG myeloma protein as a standard in ELISA or the purified IgA myeloma protein.

Salivary anti-SpaA IgA were quantified in analogous manners using affinity purified rabbit anti-mouse (α-chain specific) alkaline phosphatase conjugate as the secondary antibody. Since pilocarpine stimulation causes variable dilution of saliva, it was essential to quantitate the specific amount of anti-SpaA sIgA in saliva in comparison to total sIgA, the later determined by using the mouse myeloma IgA as a standard. Suitable positive and negative controls were used. For serum antibody, mouse sera obtained from mice immunized with purified SpaA protein obtained from recombinant E. coli were used. For positive controls for salivary secretory IgA, mice were immunized directly in the salivary glands, an immunization route known to induce high levels of sIgA specific against the immunizing antigen. It should be noted that the measurement of antibody titers in saliva make use of SpaA protein purified from recombinant E. coli. This is because the conventional mice used have antibodies against common streptococcal antigens, including lipoteichoic acid, and these contaminating antigens are difficult to separate from SpaA protein obtained from supernatant fluids of S. mutans cultures.

Table 1 shows the results of experiments on long term feeding of microorganisms expressing the SpaA protein to mice. Table 1 shows sIgA titers in saliva of mice fed E. coli which express the SpaA protein.

TABLE 1 sIgA titers in saliva of BALB/c mice fed E. coli χ2846 (pYA210) expressing SpaA protein[a]

| | Control | | | Fed χ2846 (pYA210) | | |
|---|---|---|---|---|---|---|
| Time (weeks) | Total sIgA[b] | Anti-SpaA-sIgA[b] | Percent spec. sIgA | Total sIgA[b] | Anti-SpaA-sIgA[b] | Percent spec. sIgA |
| 0 | 2023 | 2.6 | 0.13 | 3852 | 4.1 | 0.11 |
| 2 | 4913 | 3.4 | 0.17 | 4785 | 4.3 | 0.09 |
| 4 | 4249 | 3.4 | 0.08 | 5969 | 6.9 | 0.12 |
| 7 | 5400 | 3.9 | 0.07 | 5351 | 5.0 | 0.09 |
| 9 | 7046 | 4.9 | 0.07 | 5455 | 49.1 | 0.90 |
| 11 | 6994 | 6.8 | 0.10 | 6502 | 77.4 | 1.19 |
| 13 | 6428 | 17.8 | 0.28 | 4772 | 58.1 | 1.22 |
| 16 | 6351 | 4.5 | 0.07 | 8089 | 85.7 | 1.06 |
| 18 | 6825 | 5.5 | 0.08 | 9526 | 40.3 | 0.42 |
| 21 | 7891 | 7.1 | 0.09 | 7512 | 61.0 | 0.81 |
| 26.5 | 5846 | 4.2 | 0.07 | 6728 | 45.5 | 0.68 |
| 28.5 | 5904 | 3.1 | 0.05 | 7232 | 53.8 | 0.74 |

[a]E. coli χ2846 (pYA210) was heat killed, lyophilized and added to mouse meal at a concentration equivalent to $10^7$ bacteria per gram of mouse meal which was fed ad libitum. Saliva samples were collected following pilocarpine injection. Total sIgA and anit-SpaA sIgA were quantitated by ELISA.
[b]Expressed in ng/ml of saliva.

EXAMPLE 2

Agrobacterium tumefaciens-mediated transformation

I. VECTOR CONSTRUCTION

Construction of vectors such as pSUN341 and pSUN343 that are ready for transfer to A. tumefaciens are described in Example 1. The CaMV promoter—spaA-NOPS-polyA sequence, an expression cassette from a vector such as pSUN390, pSUN392, and pSUN394 (see FIG. 7) is excised from these vectors and introduced into a binary vector such as pSUN473 (FIG. 4) prior to transfer to A. tumefaciens. In each case the binary vector such as pSUN341 would be transferred to an A. tumefaciens strain possessing a disarmed Ti plasmid by triparental mating, Fraley et al., supra. This could be accomplished by use of an A. tumefaciens strain such as LBA4404 or LBA1050 possessing disarmed plasmids such as pAL4404 or pAL1050. A. tumefaciens strains containing pSUN341 and pSUN343 produced as much SpaA protein as did E. coli strains with these vectors as revealed by Western blot analysis (data not shown).

II. TRANSFORMATION

Nicotiana tobaccum, varieties Havana and Xanthi, have been transformed by A. tumefaciens containing pSUN341 and pAL4404 or pSUN343 and pAL4404 using the leaf disc transformation method (Horsch et al., supra). Briefly, axenic leaf tissues prepared as discs were dipped in a liquid culture of A. tumefaciens at a concentration of ~$10^8$ cells/ml. After allowing sufficient time for the infection to occur (5–30 sec.) the tissues were blotted dry and plated on tissue regeneration medium. After 2 or 3 days, the explant tissues were removed to fresh medium containing the antibiotics carbenicillin or cefotaxime to kill the A. tumefaciens and kanamycin to select for transformed plant cells. In tobacco, it is fairly easy to generate shoots which can form whole transgenic plants. The transformed tobacco tissue was selected and whole plants regenerated in accordance with the procedures described by Rogers et al., Methods Enzymol. 118, 627 (1986). Callus tissue was assayed for nopaline synthase activity in accordance with Otten et al., Biochem. Biophys. Acta. 527, 497 (1978). A total of 64 transgenic plants, derived from 5 separate experiments regenerated from callus tissue growing on selected media with 300 μg kanamycin/ml, were tested for the production of SpaA protein using dot blot and Western blot analyses and for production of nopaline using paper electrophoresis with a nopaline standard and a negative control plant. Only one of 64 plants produced SpaA whereas 33 of 46 tested produced nopaline. DNA was isolated from a number of plants for analysis using the Southern blot technique, Southern, J. Mol. Biol. 98, 503 (1978). By using a 2.0 kb SpaA probe, six plants tested were demonstrated to contain the SpaA gene regardless of whether they tested negative or positive for nopaline production or SpaA synthesis. Using a DNA probe for neomycin phosphotransferase to analyze restricted DNA from nine plants revealed that they all contained the neomycin phosphotransferase gene and all had DNA insertions in different regions of the tobacco genome since the flanking sequences were different in all nine instances. The one plant making SpaA protein was nopaline positive and contains the SpaA gene sequence from pSUN343.

III. Production and Stability of SpaA in Transgenic Tobacco

Figure 11:
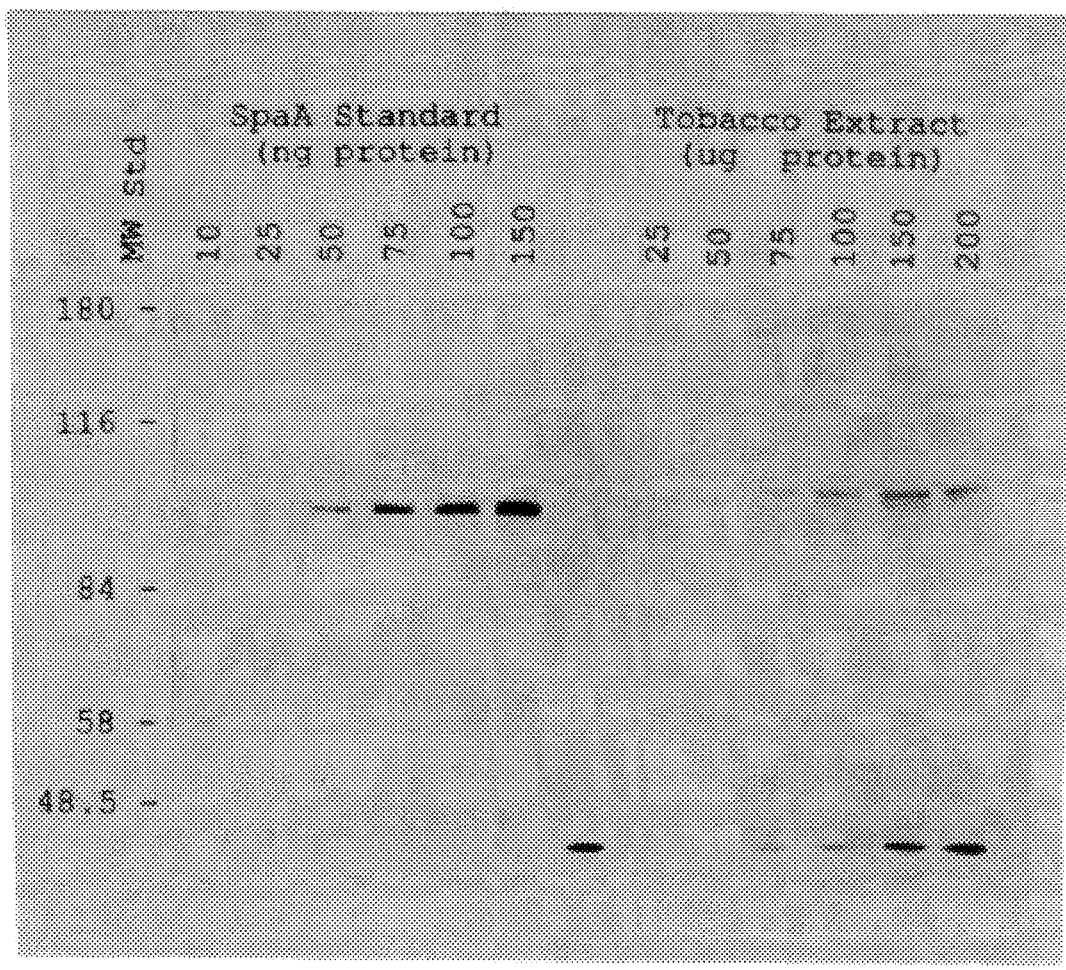
FIG. 11 illustrates densitometric quantitation of the amount of SpaA protein synthesized by transgenic tobacco plants.
Figure 12:
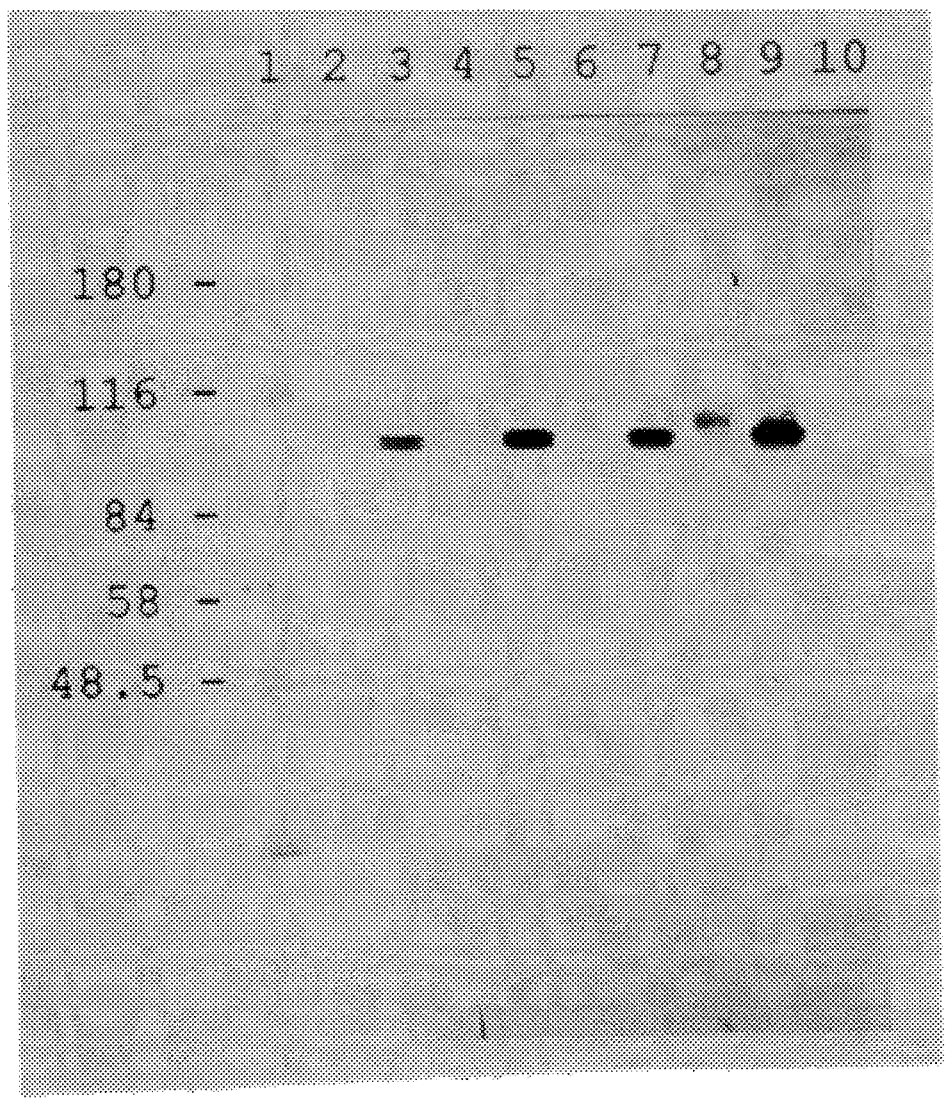
FIG. 12 illustrates the results of a Western blot analysis of a SDS polyacrylamide gel which compares samples of tobacco which produce SpaA protein to samples of tobacco which do not produce SpaA protein and also compares fresh samples, samples lyophilized and stored at −20° C., samples stored at room temperature and samples mixed with commercial mouse meal.

SpaA protein produced by E. coli containing pYA177 was purified by previously developed methods (Holt et al., supra) and following successive separation on SDS polyacrylamide gels by electroelution of the highest molecular weight SpaA band. Leaf discs from the transgenic tobacco plant producing SpaA protein were homogenized (using a Wheaton Instruments overhead stirrer containing a microfuge pestle) in 20 mm Tris pH7.4, 350 mM NaCl and 0.1% β-mercaptoethanol. The supernatant fluid was recovered after centrifugal sedimentation of debris. Protein assays were done on the purified SpaA protein and on the tobacco cell extract. Various dilutions of the Tobacco cell extract and varying amounts of purified SpaA protein in various lanes as controls were electrophoresed on SDS polyacrylamide gel. The gel was then subjected to western blot analysis using rabbit anti SpaA serum. The results of this analysis are depicted in FIG. 11. The SpaA protein produced by the transgenic tobacco has a mass of 105 kDa which is slightly less than the size of the SpaA protein made by pYA208 and pSUN343 (FIG. 6). The difference in size of the protein is probably due to processing in planta. The SpaA protein produced by the transgenic plant is a doublet and there is little or no breakdown material discernible. This is not to say that breakdown does not occur but that if it does it is degraded by the plant. The intensities of the Western blot bands were quantitated using a Molecular Dynamics densitometer. The data used to derive a standard curve are included in Table 2. Based on this, it was calculated that the SpaA protein synthesized by the transgenic tobacco plant represented 0.02% of the total plant protein.

TABLE 2

Densitometer readings of the bands shown on the Western blot depicted in FIG. 11.

| Purified SpaA (ng) | Densitometer value | Tobacco extract (µg) | Densitometer value |
|---|---|---|---|
| 10 | 145 466 | 25 | 75 423 |
| 25 | 267 154 | 50 | 169 168 |
| 50 | 696 040 | 75 | 219 917 |
| 75 | 1 044 156 | 100 | 257 764 |
| 100 | 1 205 834 | 150 | 430 530 |
| 150 | 1 534 383 | 200 | 519 636 |

IV. Heritability of the Ability to Produce the SpaA Protein

The SpaA producing tobacco plant was permitted to form seed. After seed collection and curing, 50 seedlings representing the F2 generation were obtained after seed germination and plants grown to test for heritability of the SpaA encoding sequence. Dot blot and Western blot analyses were used to detect and quantitate SpaA production. Eighteen plants did not make any SpaA protein whereas 32 did. These all produced a SpaA protein having the same molecular mass as the SpaA protein produced by the parental transgenic tobacco plants. The $\chi^2$ value is 3.23 which falls below the $\chi^2$ value for probability of 0.05 which demonstrates that the 32:18 ratio of SpaA producing to non-producing plants fits the expected 3:1 ratio of a plant heterozygous for a trait that is segregating as a single Mendelian factor.

The 32 SpaA positive plants were further analyzed by quantitative densitometric measurement of Western blot data to determine whether plants homozygous for the ability to produce SpaA could be differentiated from plants that were heterozygous for the trait. The data in Table 3 reveal that twelve of the plants produced an amount of SpaA that might be indicative of homozygosity. Six of these plants as well as six judged to be heterozygous are being grown for production of seed to determine, by analysis of germinated offspring, whether the densitometric quantitation can be relied on to indicate homozygosity versus heterozygosity.

The stability and immunogenicity analyses are performed as described above in Example 1.

TABLE 3

SpaA protein as a percentage of total protein in 32 F2 SpaA producing plants.*

| Plant # | SpaA × 100 total protein | Plant # | SpaA × 100 total protein |
|---|---|---|---|
| 2 | .043 | 25 | .008 |
| 4 | .049 | 26 | .016 |
| 6 | .038 | 27 | .026 |
| 9 | .032 | 30 | .049 |
| 11 | .035 | 31 | .023 |
| 13 | .044 | 33 | .013 |
| 14 | .008 | 34 | .011 |
| 15 | .015 | 35 | .014 |
| 17 | .022 | 37 | .026 |
| 18 | .012 | 38 | .009 |
| 19 | .002 | 39 | .015 |
| 20 | .031 | 42 | .014 |
| 21 | .038 | 43 | .009 |
| 22 | .003 | 48 | .003 |

TABLE 3-continued

SpaA protein as a percentage of total protein in 32 F2 SpaA producing plants.*

| Plant # | SpaA × 100 total protein | Plant # | SpaA × 100 total protein |
|---|---|---|---|
| 23 | .015 | 49 | .011 |
| 24 | .020 | 50 | .007 |

*Values were calculated from laser densitometer readings of a Western blot. Plants 1, 3, 5, 7, 8, 10, 12, 16, 28, 29, 32, 36, 40, 41, 44, 45, 46 and 47 did not produce any SpaA protein.

Processing of Transgenic Plant Material for Use as Animal Feed

Leaf tissue from a SpaA producing plant was removed, cut into small (approximately 3 $cm^2$) pieces and dried at 37° C. for approximately 2 days. Also, leaf tissue from a SpaA producing plant was removed, quick frozen in liquid nitrogen and lyophilized using a Vertis freezemobile II lyophilizer. In Western blot analysis the amount of SpaA protein as a percentage of total protein, from both methods, revealed little or no loss of SpaA protein. Lyophilized leaf tissue from the transgenic tobacco plant producing SpaA was stored at −20° C. and at room temperature for 13 days. Lyophilized tissue stored at room temperature for 13 days was also mixed with mouse meal at a 1:1 ratio. All samples were homogenized using a Wheaton Instruments overhead stirrer containing a microfuge pestle in 20 mM Tris pH7.4, 350 mM NaCl and 0.1% mercaptoethanol. The supernatant fluid was recovered after centrifugal sedimentation of debris followed by protein assay. Western blot analysis showed little to no loss of SpaA protein in all cases (FIG. 12). Plant samples in lanes 2, 4, 6 and 8 were from a transformed plant that contains the spaA sequence but which did not express the SpaA protein as revealed by the absence of reaction with spaA antiserum. See lanes 2 and 4. However, when stored for 13 days at room temperature something in the lyophilized plant tissue reacts weakly with the SpaA antibody as seen in lanes 6 and 8. This is not completely understood.

Immunogenicity of SpaA Protein Expressed in Plants

SpaA producing tobacco plant material processed as described above can be mixed with mouse meal at different dosages to investigate elicitation of a secretory immune response against the ingested SpaA protein. Previous results by Michalek et al., 1976, supra, observed significant sIgA production in rats given $10^8$ killed *S. mutans* cells/ml of drinking water. The SpaA protein in *S. mutans* represents approximately 0.2% of the total protein and each *S. mutans* cell contains approximately $2\times10^{-10}$ mg of protein. Thus, there are 40 nanograms of SpaA in every $10^8$ *S. mutans* cells. Based on the foregoing analysis of the heterozygous SpaA producing transgenic plant, 2 mg of dried transgenic tobacco contains 40 nanograms of SpaA protein. Mouse meal can be supplemented with 200 μg, 2 mg, and 20 mg of dried transgenic tobacco meal per gram of mouse meal. These concentrations provide oral immunization doses comparable to administering $10^7$, $10^8$ and $10^9$ *S. mutans* cells per gram of feed. For this experimental protocol, it should be noted that maximal doses of tobacco meal will constitute 2% of the mouse meal diet. 2% is 5 times less than the dosage of tobacco meal that can be tolerated by continuous consumption by mice without any noticeable adverse physiological effects.

V. Immunogenicity of SpaA Protein Expressed in Plants

This diet is fed *ad libitum* to female BALB/c mice, 9 to 10 weeks old. The mice are weighed weekly to follow their growth and development. Mice are observed visually to determine the status of their health.

Saliva samples are collected weekly. Salivation is stimulated by pilocarpine. Serum is collected biweekly using retroorbital bleeding.

Serum anti-SpaA IgG and salivary IgA are detected by ELISA. Dynatech Laboratories immulon-1 flat-bottom polystyrene plates are coated overnight at 41° C. with 100 µl (4.25 µg protein) of a 1:5 dilution in 0.1M NaHCO$_3$ buffer, pH 9.6, of semi-purified SpaA, obtained from a 70% ammonium sulfate precipitated filtered supernatant fluid from *S. mutans* followed by dialysis and lyophilization, or of SpaA purified from recombinant *E. coli*. Plates are then washed three times with phosphate buffered saline (PBS; pH 7.2) containing 0.05% Tween-20 and then blocked for 90 min. with PBS plus 0.05% Tween-20 and 1% bovine serum albumin. After washing, serum samples (100 µl of each dilution) are added and allowed to incubate overnight at 4° C. Plates are washed again and the secondary antibodies which are affinity purified goat anti-mouse IgG (γ-chain specific) or goat anti-mouse IgA (α-chain specific) conjugated with alkaline phosphatase (1:1000 dilution) added and incubated for 4 hours at room temperature. After washing, nitrophenyl phosphate substrate dissolved in diethylalamine buffer, pH 9.8, is added and plates incubated at room temperature for 1.5 hours. They are then read at 405 nm, with a Bio-Tek Automated EIA Plate Reader. Standardization of anti-SpaA serum IgG and serum IgA in comparison to total serum IgA and IgG are accomplished by use of purified mouse IgG myeloma protein as a standard in ELISA or the purified IgA myeloma protein.

Salivary anti-SpaA IgA are quantified in analogous manners using affinity purified rabbit anti-mouse (α-chain specific) alkaline phosphatase conjugate as the secondary antibody. Since pilocarpine stimulation causes variable dilution of saliva, it is essential to quantitate the specific amount of anti-SpaA sIgA in saliva in comparison to total sIgA, the later determined by using the mouse myeloma IgA as a standard. Suitable positive and negative controls are used. For serum antibody, mouse sera obtained from mice immunized with purified SpaA protein obtained from recombinant *E. coli* are used.

EXAMPLE 3

Plant Transformation

I. Construction of Vectors

Vector pSUN343 described in Example 1 containing the SpaA sequence is used.

II. Plant Transformation by Electroporation

The procedure used to electroporate tobacco protoplasts is essentially as described by David Cheng and co-workers in the Hoefer Scientific Instruments Technical Bulletin #118. The upper epidermis of tobacco leaves (*Nicotiana tobacum* c.v. *Havana*) isolated when 3 or 4 cm in length from in vitro grown plants, is brushed with 320 grit aluminum oxide powder to permit the infiltration of cell wall degradative enzymes used to prepare protoplasts by the method of Magnien, E. et al., *Acta Genetica Sinica* 7, 231 (1980). Enzymatically released protoplasts are washed with 17.5% sucrose, floated and harvested by centrifugation for 5 min. at 300×g in a 60 ml Babcock bottle. Linearized or supercoiled DNA (pSUN343) is mixed with the protoplasts in a final volume of 0.5 ml at a concentration of 0.1 mg/ml and 7×10$^5$ cells/ml respectively, in a 16 mm diameter Nunc Multidish well. A single pulse is administered at room temperature (23° C.) with a Hoefer PG 101 ProGenetor electroporation unit using a PG120-2.5 electrode for 10 msec at 200 V. Electroporated protoplasts are kept stationary for 10 min. prior to the addition of 1 ml of culture medium. Cells were subsequently diluted to a final concentration of 10$^5$ cells/ml. These cells may then be assayed for transient expression of the spaA gene after a period of 40–48 hours or, depending on the DNA construct used, plated to generate callus tissues under kanamycin selection, followed by regeneration to whole plants.

III. Regeneration

Post-transformation protoplasts are plated on callus proliferation medium with kanamycin as selection pressure and cultured for 2–3 weeks at 24° C. in a 16 hour diffused light/8 hour dark cycle. Callus is subcultured every 2–3 weeks to produce enough tissue to proceed with regeneration. After enough tissue is obtained, the callus is transferred to regeneration medium with or without selection pressure and cultured for 3–4 weeks at 24° C. in a 16 hour diffused light/8 hour dark cycle until shoot bud formation. At this time, the material is transferred to plant establishment medium with or without selection pressure and cultured at 24° C. in a 16 hour diffused light/8 hour dark cycle until 3–4 leaves formed. The plantlet is then transferred to soil.

The callus tissue and regenerated plants can be evaluated for level of SpaA protein, relative to total protein by ELISA or by Western blot and quantitative densitometer analysis. (See Tables 2 and 3).

IV. Stability, Heritability and Immunogenicity of SpaA Protein Expressed in Plants Stability, heritability and immunogenicity of SpaA protein in transformed plants are analyzed by the method of Examples 1 and 2.

EXAMPLE 4

Example 2 is repeated except that in step I a suitable plant transformation vector containing the gtfB gene is constructed. For example, pSUN387 (gtfB) is prepared which contains the gtfB gene isolated from pSU20 (Shiroza, T. et al., supra) in place of the spaA gene. The gtfB encoding sequence along with the CaMV 355 promoter and NOPS 3' polyA sequence is introduced into an appropriate binary vector such as pSUN473 or pSUN475.

Following generation of transgenic tobacco plants, stability, heritability and immunogenicity analyses for GtfB protein are performed as described in Examples 1 and 2.

EXAMPLE 5

Example 3 is repeated except that in step I a vector containing both spaA and gtfB is constructed. For example, gtfB is inserted to follow the spaA sequence in pSUN394. In this way a construct expressing two colonization antigens is formed.

Following generation of transgenic plants from protoplast-derived callus, stability, heritability and immunogenicity of SpaA and GtfB proteins are analyzed as described in Examples 1 and 2.

EXAMPLE 6

Example 3 is repeated except that in step I a suitable plant transformation vector containing the dextranase gene is constructed. For example, pSUN387 is prepared which contains the dextranase (dex) gene isolated from pYA993.

Following generation of transgenic plants from protoplast-derived callus, stability, heritability and immunogenicity of dextranase protein are analyzed as described in Examples 1 and 2.

EXAMPLE 7

Example 3 is repeated except that in step I a suitable plant transformation vector containing both spaA and dex is constructed. For example, dex is inserted to follow the spaA sequence in pSUN394. In this way a construct expressing two colonization antigens is formed.

Following generation of transgenic plants from protoplast-derived callus material, stability, heritability and immunogenicity of SpaA and dextranase proteins are analyzed as described in Examples 1 and 2.

EXAMPLE 8

Example 3 is repeated except that in step I a suitable plant transformation vector containing the K88 pilus colonization antigen gene is constructed. For example, pSUN387 is prepared which contains the K88 pilus colonization antigen isolated from plasmid pMK005, which was developed by Kehoe et al., Nature 291, 122 (1981). Following generation of transgenic plants from protoplast-derived callus material, stability, heritability and immunogenicity analyses of K88 antigen are performed as described in Examples 1 and 2.

EXAMPLE 9

Example 3 is repeated except that in step I a suitable plant transformation vector containing the K99 pilus colonization antigen gene is constructed. For example, pSUN387 is prepared which contains the K99 pilus colonizations antigen gene isolated from plasmid pRI9906. Following generation of transgenic plants from protoplast-derived callus material, stability, heritability and immunogenicity analyses of K99 antigen are performed as described in Examples 1 and 2.

EXAMPLE 10

Example 3 is repeated except that the plant transformation vector is the plasmid pSUN387 (spaA/LT-B) containing a DNA sequence which codes for a fusion protein comprising the SpaA protein and the LT-B protein. The LT-B sequence is the N-terminus of the fusion protein. A DNA sequence coding for the LT-B protein is isolated from E. coli (Yamamoto, T and Yokoto, T., supra). Following generation of transgenic plants from protoplast-derived callus material, stability, heritability and immunogenicity analyses of SpaA and LT-B proteins are performed as described in Examples 1 and 2.

EXAMPLE 11

Example 2 is repeated except that plant transformation using pSUN473 (gtfB) was carried out on tomato according to Fillatti, J. et al., (1987), supra. Following generation of whole plants from selected explant tissues, stability, heritability and immunogenicity analyses of gtfB are performed as described in Examples 1 and 2.

EXAMPLE 12

Example 2 is repeated except that plant transformation using pSUN475 (LT-B) was carried out on sunflower according to Everett, N. P. et al., (1987), supra. Following generation of whole plants from selected explant tissues, stability, heritability and immunogenicity analyses of LT-B protein are performed as described in Examples 1 and 2.

EXAMPLE 13

Example 2 is repeated except that plant transformation using pSUN473 (K99) was carried out on soybean according to Hinchee, M. A. et al., (1987), supra. Following generation of whole plants from selected explant tissues, stability, heritability and immunogenicity analyses of K99 protein are performed as described in Examples 1 and 2.

EXAMPLE 14

Example 2 is repeated except that plant transformation using pSUN473 (K88) was carried out on potato according to Facciotti, D. et al., (1985), supra. Following generation of whole plants from selected explant tissues, stability, heritability and immunogenicity analyses of K88 antigen are performed as described in Examples 1 and 2.

EXAMPLE 15

Plant transformation is carried out by microinjection on alfalfa.

Transfer of pSUN387 (K99) into plant cells is achieved by injection of a solution of plasmid DNA with a finely pulled glass needle directly into isolated protoplasts, cultured cells and tissues as described Reich, T. J. et al., Bio/Technology 4, 1001, (1986); Can.J.Bot. 64, 1259, (1986) and injection into meristematic tissues of seedlings and plants as described by De La Pena, A. et al., Nature 325, 274, (1987), Graves, A. C. et al., Plant Mol. Biol. 7, 763, (1984).

Stability, heritability and immunogenicity analyses of K99 protein are performed as described in Examples 1 and 2.

EXAMPLE 16

Plant transformation is carried out by application of polyethylene glycol on tobacco according to Negrutiu, R. et al., (1987), supra. The DNA used is linearized plasmid pSUN390.

The protoplasts are suspended in 0.5M mannitol containing 15 mM $MgCl_2$ at a density of about $2 \times 10^6$ per ml. The protoplast suspension is distributed into 10 ml plastic centrifuge tubes. The DNA is added and then the PEG solution added [40% (w/v MW 4000 in 0.4 M mannitol, 0.1M $Ca(NO_3)_2$, (pH 7.0)]. The solutions are mixed gently and incubated for 30 minutes at room temperature (about 24° C.) for 30 minutes with occasional shaking. Wash solution is then added, and the contents of the tube gently mixed. The wash solution consists of 87 nM mannitol, $CaCl_2$, $MgCl_2$, KC 1, Tris/HCl and m-inositol, (pH 9.0). Four further aliquots of wash solution are added at 4 minute intervals, with mixing after each addition. The tube is then centrifuged at about 60 g for about 10 minutes, and the supernatant discarded. The sedimented protoplasts are taken up in culture medium, and placed in a 10 cm petri dish.

Stability, heritability and immunogenicity analyses of SpaA protein are performed as described in Examples 1 and 2.

EXAMPLE 17

Example 16 is repeated except that in step II plant transformation pSUN387 (K88) is carried on Lolium multiflorum according to Negrutiu, R. et al., (1987), supra. Stability, heritability and immunogenicity analyses of K88 protein are performed as described in Examples 1 and 2.

EXAMPLE 18

Transformation of Rice by Electroporation

DNA transfer and selection of transformants. Protoplasts are isolated from anther-derived cell suspensions of rice (*Oryza sativa*), and electroporated according to Fromm et al., with some modification, as follows. Protoplasts ($2 \times 10^5$) and circular-form plasmid such as pSUN390, pSUN391, pSUN392, pSUN393 and pSUN394 (10 µg each) are suspended in 0.6 ml of a buffer consisting of 0.5 mM 2-[N-Morpholino]ethanesulfonic acid (pH5.8), 7 mM KCl, 4 mM $CaCl_2$-$2H_2O$ and 6.5% mannitol in a plastic cuvette (interelectrode distance was 0.4 cm). An electrical pulse is delivered from a 125 µF capacitor charged at 500 V/cm (Gene-Pulser, Bio-Rad, Calif. USA). The resistance-capacitance (RC) time-constants are 4 msec and 20 msec, respectively. After 10 min at 4° C., followed by 10 min at room temperature, electroporated protoplasts are transferred to a petri-dish (5 cm in diameter) containing 2.5 ml B5 medium supplemented with 2 mg/l 2,4-dichlorophenoxyacetic acid (2,4-D) and 5% mannitol. After 2 weeks, 1 ml $NO_3$ medium (B5 medium without ammonium sulphate)supplemented with 2 mg/l 2,4-D and 3% glucose is added. After 3 weeks, the medium is replaced by $NO_3$ medium lacking glucose, and containing 2 µg/ml G418 sulphate (Schering Co., N.J.). One month after electroporation, surviving microcalli are transferred to $NO_3$ medium containing 20 µg G418/ml and 1% agarose (Sigma type I). After another 2 weeks, growing calli are transferred onto N6 medium containing 0.2 mg/l indole-3-acetic acid, 1 mg/l kinetin and 1% agarose (regeneration medium). Callus tissue is assayed for nopaline synthase activity in accordance with Otten et al., supra.

Stability, heritability and immunogenicity analyses of SpaA protein are performed as described in Examples 1 and 2.

EXAMPLE 19

Stable Transformation of Soybean by Particle Acceleration

Another method to introduce foreign DNA sequences into plant cells comprises the attachment of said DNA to tungsten particles which are then forced into plant cells by means of a shooting device as described by Klein, T. M. et al., supra or by means of particle acceleration using a finely tuned electric discharge to accelerate DNA coated gold particles as described by McCabe, E. T. et al., supra. Any plant tissue or plant organ may be used as the target for this procedure, including but not limited to embryos, apical and other meristems, buds, somatic and sexual-tissues in vivo and in vitro. Transgenic cells and callus are selected following established procedures known in the art. Targeted tissues are induced to form somatic embryos or regenerate shoots to give transgenic plants according to established procedures known in the art. The appropriate procedure may be chosen in accordance with the plant species used.

The regenerated plant may be chimeric with respect to the incorporated foreign DNA. If the cells containing the foreign DNA develop into either micro-/or macrospores, the integrated foreign DNA will be transmitted to sexual progeny. If the cells containing the foreign DNA are somatic cells of the plant, non-chimeric transgenic plants are produced by conventional methods of vegetative propagation either in vivo, i.e. from buds or stem cuttings, or in vitro following established procedures known in the art. Such procedures may be chosen in accordance with the plant species used.

Transformation is carried out on soybean according to McCabe, D. E. et al., (1988), supra.

DNA preparation. DNA coated projectiles are prepared by mixing 1.5–3 µm gold spheres (Alfa Chemical Co.) with a solution of pSUN387 (gtfB) DNA at a rate of 1 mg gold beads per 1 µg of DNA. The slurry is dried under a stream of $N_2$, and the dry pellet resuspended in 100% ethanol at a concentration of 2 mg beads per ml. 162 µl of the gold suspension is pipetted onto an 18 mm square of aluminized plastic film. The sheet, now carrying a thin layer of beads, is air dried.

Particle acceleration. Embryonic axes with their primary leaves removed to expose the meristem, are subjected to particle acceleration. The sheet bearing the beads is loaded onto a particle accelerating machine, which uses the discharge of a high voltage capacitor through a small water droplet as the motive force. A 100-mesh retaining screen is placed between the sheet and the target tissue suspended above the machine. The assembly is then evacuated to about 500 mm Hg to reduce aerodynamic drag. Fourteen kV from a 2 µF capacitor is discharged through a 10 µl water drop inside the polyvinyl chloride expansion chamber. The sheet is blown against the retaining screen permitting the beads to continue onward to impact the target tissues suspended above the screen. The target axes are positioned on a water agar plate so that, when the plate is inverted over the screen, the meristematic regions are positioned in the path of the accelerated beads.

Plant regeneration. Plant tissue treated by particle acceleration are plated on modified MS media supplemented with 13.3 µM benzylaminopurine, 0.2 µM naphthalene acetic acid, 5 µM thiamine and 12 mM proline and incubated in the dark for 1–2 weeks, at room temperature. The axes are then transferred to fresh MS media supplemented with 1.7 µM benzylaminopurine and 0.2 µM indolyl-3-butyric acid. Plant regeneration is allowed to proceed by continuous incubation of the axes under a 16 h photoperiod. Multiple shoots are formed from both the primary and axillary meristems.

Excised shoots are rooted for further growth by plating them on plant regeneration medium.

Stability, heritability and immunogenicity analyses of GtfB protein are performed as described in Examples 1 and 2.

While the invention has been disclosed by reference to the details of preferred embodiments, the disclosure is intended in an illustrative rather than in a limiting sense, as it is contemplated that modifications will readily occur to those skilled in the art, within the spirit of the invention and the scope of the appended claims.

What is claimed is:

1. A method of making a composition suitable for eliciting a secretory immune response in a human or other animal, said composition comprising a transgenic plant or transgenic plant tissue obtained from said transgenic plant which comprises and expresses a DNA sequence coding for an antigen or antigenic determinant of a pathogenic microorganism, said antigen or antigenic determinant being capable of eliciting a secretory immune response upon oral administration of said transgenic plant or said transgenic plant tissue, wherein the method comprises the step of mixing said transgenic plant or said transgenic plant tissue with a food substance.

2. The method of claim 1 wherein said antigen is from *Streptococcus mutans* or *Escherichia coli*.

3. The method of claim 1 wherein the antigen is selected from the group consisting of SpaA, GtfB, dextranase, K88, K99, CFA, LT-B or an antigenic determinant thereof.

4. The method of claim 1 wherein the transgenic plant is dicotyledonous.

5. The method of claim 1 wherein the transgenic plant is monocotyledonous.

* * * * *

UNITED STATES PATENT AND TRADEMARK OFFICE
CERTIFICATE OF CORRECTION

PATENT NO. : 5,654,184  
DATED : August 5, 1997  
INVENTOR(S) : Roy Curtiss, III and Guy A. Cardineau Page 1 of 2

It is certified that error appears in the above-identified patent and that said Letters Patent is hereby corrected as shown below:

Column 2, line 15: "Et al.," should read --et al.,--.

Column 5, line 41: "Sihackaki, D." should read --Sihachaki, D.--.

Column 11, line 35: "pigs calves, and" should read --pigs, calves, and--;

lines 37-38: "swine feed, K99 pilus colonization antigen for humans." should read --swine feed, K99 pilus colonization antigen for calf feed, and the CFA pilus colonization antigen for humans.--.

Column 13, line 54: "deFramon, A." should read --deFramond, A.--.

Column 17, line 27: "Maniantis, T." should read --Maniatis, T.--.

Column 19, line 23: "DNYP's" should read --dNTP's--.

Column 20, line 17: "Sca-I-AsuII" should read --*ScaI-AsuII*--.

UNITED STATES PATENT AND TRADEMARK OFFICE
CERTIFICATE OF CORRECTION

PATENT NO. : 5,654,184
DATED : August 5, 1997
INVENTOR(S) : Roy Curtiss, III and Guy A. Cardineau It is certified that error appears in the above-identified patent and that said Letters Patent is hereby corrected as shown below:

Column 23, line 43: "anit-SpaA" should read --anti-SpaA--.

Column 30, line 45: "KC 1," should read --KC1,--.

Signed and Sealed this

Ninth Day of December, 1997

Attest:

BRUCE LEHMAN

Attesting Officer

Commissioner of Patents and Trademarks